US010954505B2

(12) United States Patent
Jaeckel et al.

(10) Patent No.: US 10,954,505 B2
(45) Date of Patent: *Mar. 23, 2021

(54) VARIANTS OF CHYMOSIN WITH IMPROVED MILK-CLOTTING PROPERTIES

(71) Applicant: CHR. HANSEN A/S, Hoersholm (DK)

(72) Inventors: Christian Jaeckel, Vaerloese (DK);
Martin Lund, Copenhagen (DK);
Johannes Maarten Van Den Brink,
Herlev (DK)

(73) Assignee: CHR. HANSEN A/S, Hoersholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/302,584

(22) PCT Filed: May 19, 2017

(86) PCT No.: PCT/EP2017/062086
§ 371 (c)(1),
(2) Date: Nov. 16, 2018

(87) PCT Pub. No.: WO2017/198810
PCT Pub. Date: Nov. 23, 2017

(65) Prior Publication Data
US 2019/0116821 A1    Apr. 25, 2019

(30) Foreign Application Priority Data
May 19, 2016    (EP) .................................. 16170411

(51) Int. Cl.
*C12N 9/48* (2006.01)
*C12N 9/64* (2006.01)
*A23C 19/04* (2006.01)
*A23C 19/068* (2006.01)
*A23C 19/072* (2006.01)
(Continued)

(52) U.S. Cl.
CPC .... *C12N 9/6483* (2013.01); *C12Y 304/23004* (2013.01); *A23C 9/1209* (2013.01); *A23C 19/04* (2013.01); *A23C 19/0684* (2013.01); *A23C 19/072* (2013.01); *A23C 19/076* (2013.01)

(58) Field of Classification Search
CPC .................................................... C12N 9/6483
See application file for complete search history.

(56) References Cited

U.S. PATENT DOCUMENTS

| 7,390,936 B1 | 6/2008 | Rooijen et al. |
| 7,482,148 B2 | 1/2009 | Mule et al. |
| 9,930,899 B2 | 4/2018 | Van Den Brink et al. |

(Continued)

FOREIGN PATENT DOCUMENTS

| EP | 0 123 928 A2 | 11/1984 |
| JP | 2010-046034 A | 3/2010 |

(Continued)

OTHER PUBLICATIONS

Studer. Residue mutations and their impact on protein structure and function: detecting beneficial and pathogenic changes. Biochem. J. (2013) 449, 581-594 (Year: 2013).*

(Continued)

*Primary Examiner* — Yong D Pak
(74) *Attorney, Agent, or Firm* — Foley & Lardner LLP

(57) ABSTRACT

Variants of chymosin with improved milk clotting properties.

19 Claims, 4 Drawing Sheets

Figure 2:
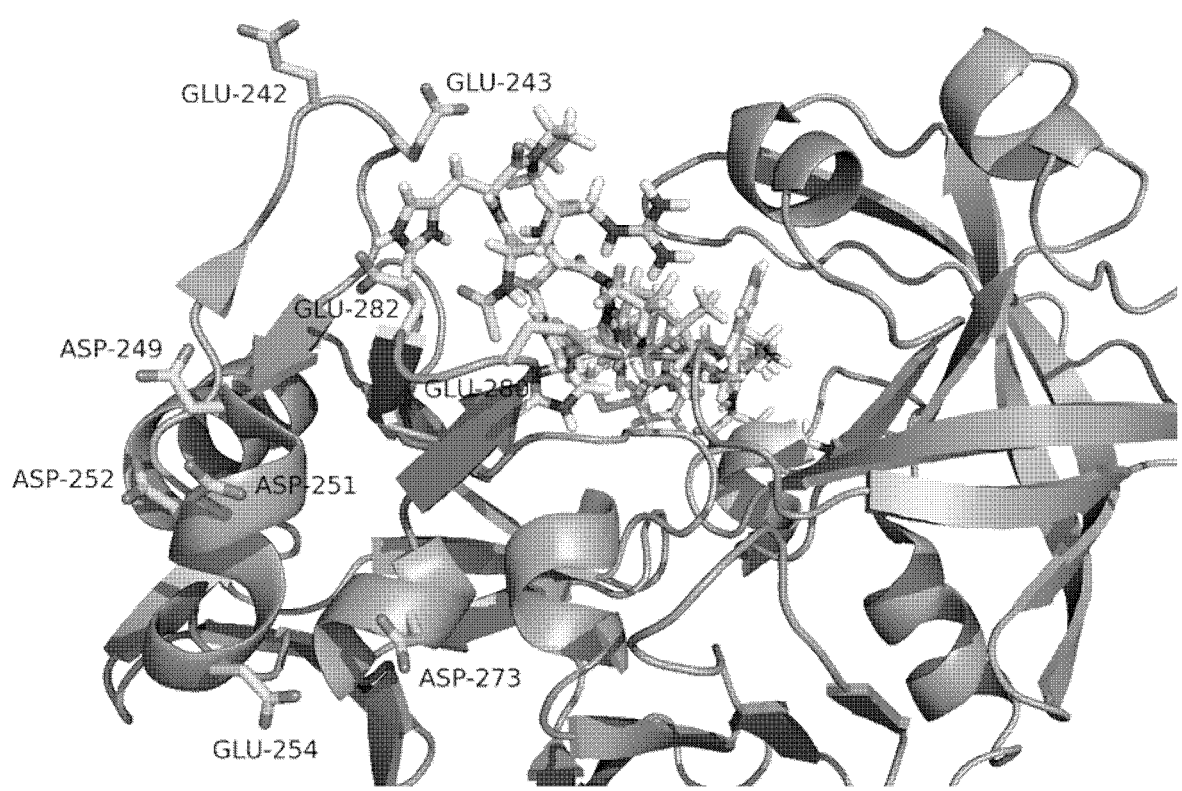

Specification includes a Sequence Listing.

(51) Int. Cl.
  *A23C 19/076* (2006.01)
  *A23C 9/12* (2006.01)

(56) References Cited

U.S. PATENT DOCUMENTS

| | | | |
|---|---|---|---|
| 10,167,463 B2* | 1/2019 | Dekker | C12Y 304/23004 |
| 2008/0226768 A1 | 9/2008 | Kappeler et al. | |
| 2011/0287137 A1 | 11/2011 | Kappeler et al. | |
| 2015/0140169 A1* | 5/2015 | Dekker | C12Y 304/23004 |
| | | | 426/36 |
| 2015/0173383 A1 | 6/2015 | Van Den Brink et al. | |
| 2017/0067041 A1 | 3/2017 | Van Den Brink et al. | |
| 2018/0110234 A1 | 4/2018 | Faiveley et al. | |
| 2018/0187179 A1 | 7/2018 | Jaeckel et al. | |
| 2018/0251747 A1 | 9/2018 | Jaeckel et al. | |
| 2018/0317510 A1 | 11/2018 | Van Den Brink et al. | |
| 2019/0174783 A1 | 6/2019 | Jaeckel et al. | |

FOREIGN PATENT DOCUMENTS

| | | | |
|---|---|---|---|
| JP | 2010-099082 A | 5/2010 | |
| JP | 2011-182794 A | 9/2011 | |
| RU | 2 192 137 C2 | 11/2002 | |
| WO | WO 02/36752 | 5/2002 | |
| WO | WO 2004/031733 A2 | 4/2004 | |
| WO | WO 2005/003345 A2 | 1/2005 | |
| WO | WO 2008/098973 | 8/2008 | |
| WO | WO 2010/110464 A1 | 9/2010 | |
| WO | WO-2013/164479 A2 | 11/2013 | |
| WO | WO 2013/164481 | 11/2013 | |
| WO | WO-2013/174840 A1 | 11/2013 | |
| WO | WO-2013164481 A1 * | 11/2013 | ........... A23C 19/072 |
| WO | WO-2015/128417 A1 | 9/2015 | |
| WO | WO-2016/207214 A1 | 12/2016 | |
| WO | WO-2017/037092 A1 | 3/2017 | |

OTHER PUBLICATIONS

U.S. Appl. No. 16/302,590, filed Nov. 16, 2018, Jaeckel et al.
U.S. Appl. No. 61/642,095, filed May 3, 2012, Dekker et al.
Albert et al., "Protein Engineering Aspartic Proteinases: Site-Directed Mutagenesis, Biochemical Characterisation, and X-Ray Analysis of Chymosins with Substituted Single Amino Acid Substitutions and Loop Replacements," in Aspartic Proteinases, Chapter 23, pp. 169-178 (1998) (James, ed.).
Bansal et al., "Suitability of recombinant camel (*Camelus dromedarius*) chymosin as a coagulant for Cheddar cheese," International Dairy Journal 19 (2009) 510-517.
Claverie-Martin et al., "Aspartic Proteases Used in Cheese Making," in Industrial Enzymes pp. 207-219 (2007) (J. Polaina and A.P. MacCabe, eds.).
Chen et al., "Functional Implications of Disulfide Bond, Cys206-Cys210, in Recombinant Prochymosin (Chymosin)," Biochemistry 2000, 39, 12140-12148 (Published online Sep. 2000).
Kappeler et al. "Compositional and Structural Analysis of Camel Milk Proteins with Emphasis on Protective Proteins," ETH Zurich Research Collection, Dissertation, ETH No. 12947, pp. 1-137 (1998).
Moller et al., "Comparison of the Hydrolysis of Bovin k-Casein by Camel and Bovine Chymosin: A Kinetic and Specificity Study," Journal of Agricultural and Food Chemistry, 60(21):5454-5460 (May 2012) (with NCBI extract).
Børsting et al., "Impact of selected coagulants and starters on primary proteolysis and amino acid release related to bitterness and structure of reduced-fat Cheddar cheese", Dairy Sci. & Technol. (Oct. 2012) vol. 92, pp. 593-612.
Creamer et al., "Rheological Evaluation of Maturing Cheddar Cheese", Journal of Food Science (1982) vol. 47, pp. 631-636.
Ehren et al., "Protein engineering of improved prolyl endopeptidases for celiac sprue therapy", Protein Engineering, Design & Selection (Oct. 2008) vol. 21, No. 12, pp. 699-707.
Filippovich et al. "Radicals," pp. 38-43 (2005).
Govindarajan et al., "Mapping of Amino Acid Substitutions Conferring Herbicide Resistance in Wheat Glutathione Transferase", ACS Synthetic Biology (Jun. 2014) vol. 4, pp. 221-227.
Gustchina et al., "Post X-ray crystallographic studies of chymosin: the existence of two structural forms and the regulation of activity by the interaction with the histidine-proline cluster of k -casein", FEBS Letters (1996) vol. 379 pp. 60-62.
Kumar et al., "Chymosin and other milk coagulants: sources and biotechnological interventions", Critical Reviews in Biotechnology (2010) vol. 30 No. 4, pp. 243-258.
McSweeney "Biochemistry of cheese ripening", International Journal of Dairy Technology, (2004) vol. 57, No. 2/3, pp. 127-144.
Moynihan et al., "Effect of camel chymosin on the texture, functionality, and sensory properties of low-moisture, part-skim Mozzarella cheese", J. Dairy Sci. (2013) vol. 97, pp. 85-96.
Newman et al., "X-ray Analyses of Aspartic Proteinases IV Structure and Refinement at 2•2 Å Resolutions of Bovine Chymosin", J. Mol. Biol. (1991) vol. 221, pp. 1295-1309.
Palmer et al., "Bovine Chymosin: A Computational Study of Recognition and Binding of Bovine k -Casein", Biochemistry (Feb. 2010) vol. 49, pp. 2563-2573.
Schechter et al., "On the Size of the Active Site in Proteases", Biochemical and Biophysical Research Communications (1967) vol. 27, No. 2 pp. 157-162.
Sørensen et al., "Hot-Spot Mapping of the Interactions between Chymosin and Bovine k -Casein", Journal of Agricultural and Food Chemistry (Jul. 2013) vol. 61, pp. 7949-7959.
Visser et al., "Peptide substrates for chymosin (rennin)" Biochem. J. (1987) vol. 244, pp. 553-558.
Beppu,et al., "Modification of Milk-clotting aspartic proteases, chymosin and mucor rennin," *GBF Monographs*, pp. 87-92 (Dec. 1989).
Brenden et al., "Introduction to Protein Structure," Garland Publishing., Inc. New York, p. 247, 1991.
Chitpinityol, et al.; "Site-specific mutations of calf chymosin B which influence milk-clotting activity"; *Food Chemistry*, 62(2): 133-139 (Jun. 1998).
Database UniProt [Online] Oct. 1, 2000 (Oct. 1, 2000),"SubName: Full=Prochymosin {ECO:0000313|EMBL:AAF27315.1};", retrieved from EBI accession No. UNIPROT:Q9N1P5 Database accession No. Q9N1P5.
Database UniProt [Online] Feb. 5, 2008 (Feb. 5, 2008), "SubName: Full=Preprochymosin b {ECO:0000313|EMBL:ABX55935.1}; EC=3. 4.23.4 {ECO:0000313|EMBL:ABX55935.1};", retrieved from EBI accession No. Uniprot:A9LY78 Database accession No. A9LY78;—& Juan Andres.
Database UniProt [Online] Nov. 1, 1990 (Nov. 1, 1990), "RecName: Full=Chymosin; EC=3.4.23.4; AltName: Full=Preprorennin; Flags: Precursor;", retrieved from EBI accession No. Uniprot:P18276 Database accession No. P18276 ;—& J. Pungercar et al: "Complete primary structure of lamb preprochymosin deduced from cDNA", Nucleic Acids Research, vol. 18, No. 15, Aug. 11, 1990 (Aug. 11, 1990), pp. 4602-4602, XP055314297, GB ISSN: 0305-1048, DOI: 10.1093/nar/18.15.4602.
Database UniProt [Online] Mar. 20, 2007 (Mar. 20, 2007), "SubName: Full=Preprochymosin {ECO:0000313|EMBL:ABN13683.1};", retrieved from EBI accession No. Uniprot:A3F4M4 Database accession No. A3F4M4.
Database Geneseq [Online] Jan. 2, 2014 (Jan. 2, 2014), "Bovine derived mature chymosin B variant H76Q.", retrieved from EBI accession No. GSP:BAY37837 Database accession No. BAY37837;—& WO 2013/164479 A2 (DSM IP Assets BV [NL]) Nov. 7, 2013 (Nov. 7, 2013).
E2R9E5_CANLF. UnitProtKB Database. 2014.
Gilliland et al.; "The Three-Dimensional Structure of Recombinant Bovine Chymosin at 2.3 Å Resolution"; *Proteins: Structure, Function, and Genetics*; 8(1): 82-101 (Jan. 1990).
Houen, et al., "The Primary Structure and Enzymic Properties of Porcine Prochymosin and Chymosin," *Int. J. Biochem. Cell Biol.*, vol. 28, No. 6, pp. 667-675 (1996).

(56) References Cited

OTHER PUBLICATIONS

Jensen et al.; "Camel and bovine chymosin: the relationship between their structures and cheese-making properties"; *Acta Crystallographica*; 69(5): 901-913 (May 2013)(published online Apr. 2013).
Kageyama, "New World Monkey Pepsinogens A and C, and Prochymosins, Purification, Characterization of Enzymatic Properties, cDNA Cloning, and Molecular Evolution," *Journal of Biochemistry*, vol. 127, pp. 761-770 (Feb. 2000).
Kappeler et al., "Characterization of recombinant camel chymosin reveals superior properties for the coagulation of bovine and camel milk," Biochemical and Biophysical Research Communications, 342 (2006) 647-654.
Lavallie, "Production of Recombinant Proteins in *Escherichia coli*," Current Protocols in Protein Science (1995) 5.1.1-5.1.8.
Lindblad-Toh et al., "Genome sequence, comparative analysis and haplotype structure of the domestic dog," Nature 438: 803-819 (2009).
Pitts et al.; "Expression and characterisation of chymosin pH optima mutants produced in *Trichoderma reesei*"; *Journal of Biotechnology*, 28(1): 69-83 (Mar. 1993).
Preprochymosin b, A9LY78,UniProt, May 16, 2012, [searched on Mar. 17, 2017]. URL: https://www.uniprot.org/A9LY78.txt?version=21.
Pungerčar et al., "Complete primary structure of lamb prepochymosin deduced from cDNA," Nucleic Acids Research, vol. 18, No. 15:4602 (Aug. 1990).
Sambrook et al., Molecular Cloning, 1989, Cold Spring Harbor Laboratory Press, pp. 8.46-8.52 and pp. 11.2-11.19.
Strop et al.; "Engineering Enzyme Subsite Specificity: Preparation, Kinetic Characterization, and X-ray Analysis at 2.0-Å Resolution of Val111Phe Site-Mutated Calf Chymosin"; *Biochemistry*, 29: 9863-9871 (Oct. 1990).
Suzuki et al.; "Alteration of catalytic properties of chymosin by site-directed mutagenesis"; *Protein Engineering*, 2(7): 563-569 (May 1989).
Suzuki et al.; "Site-directed mutagenesis reveals functional contribution of Thr218, Lys220 and Asp 304 in chymosin"; *Protein Engineering*, 4(1): 69-71 (Oct. 1990).
Vallejo et al., "Cloning and Expression of Buffalo Active Chymosin in Pichia pastoris," *J. Agric. Food Chem.*, vol. 56, No. 22, pp. 10606-10610 (Nov. 2008).
Van Den Brink et al.; "Increased production of chymosin by glycosylation"; *Journal of Biotechnology*, 125(2): 304-310 (Sep. 2006)(published online Apr. 2006).
Williams et al.; "Mutagenesis, biochemical characterization and X-ray structural analysis of point mutants of bovine chymosin"; *Protein Engineering*; 10(9): 991-997 (Sep. 1997).
Zhang et al.; "Functional implications of disulfide bond, Cys45-Cys50, in recombinant prochymosin"; *Biochimica et Biophysica Acta*, 1343(2): 278-286 (Dec. 1997).
Møller, et al., "Camel and Bovine Chymosin Hydrolysis of Bovine αs1- and β3-Caseins Studied by Comparative Peptide Mapping," *Journ. of Agriculture and Food Chemistry*, vol. 60, No. 45, pp. 11421-11432 (Oct. 2012).
V. V. Starovoitova et al. "Comparative Investigation of Functional Properties of Calf Chymosin and its Recombinant Forms," Biohimiya, 2006, tom 71, vyp. 3, s. 402-407 (in Russian).

* cited by examiner

Figure 1

```
                           1                                                    50
     Bos_bovis_chymosin_B  MRCLVVLLAV FALSQGAEIT RIPLYKGKSL RKALKEHGLL EDFLQKQQYG
                    Sheep  MRCLVVLLAV FALSQGAEIT RIPLYKGKPL RKALKERGLL EDFLQKQQYG
             C._bactrianus MRCLVVLLAA LALSQASGIT RIPLHKGKTL RKALKERGLL EDFLQRQQYA
        Camelus_dromedarius MRCLVVLLAA LALSQASGIT RIPLHKGKTL RKALKERGLL EDFLQRQQYA
                      Pig  .IRGRVLLAV LALSQGSGIT RVPLRKGKSL RKELKERGLL EDFLQKQPYA
                      Rat  MRCFVLLLAV LAIAQSHVVT RIPLHKGKSL RNTLKEQGLL EDFLRRHQYE 51                                                   100
     Bos_bovis_chymosin_B  ISSKYSGFGE VASVPLTNYL DSQYFGKIYL GTPPQEFTVL FDTGSSDFWV
                    Sheep  VSSEYSGFGE VASVPLTNYL DSQYFGKIYL GTPPQEFTVL FDTGSSDFWV
             C._bactrianus VSSKYSSLGK VAREPLTSYL DSQYFGKIYL GTPPQEFTVV FDTGSSDLWV
        Camelus_dromedarius VSSKYSSLGK VAREPLTSYL DSQYFGKIYI GTPPQEFTVV FDTGSSDLWV
                      Pig  LSSKYSSFGE VASEPLTNYL DTQYFGKIYI GTPPQEFTVV FDTGSSELWV
                      Rat  FSEKNSNIGM VASEPLTNYL DSEYFGLIYV GTPPQEFKVV FDTGSSELWV 101                                                  150
     Bos_bovis_chymosin_B  PSIYCKSNAC KNHQRFDPRK SSTFQNLGKP LSIHYGTGSM QGILGYDTVT
                    Sheep  PSIYCKSNAC KNHQRFDPRK SSTFQNLGKP LSIRYGTGSM QGILGYDTVT
             C._bactrianus PSIYCKSNAC KNHHRFDPRK SSTFRNLGKP LSIHYGTGSI EGFLGYDTVT
        Camelus_dromedarius PSIYCKSNVC KNHHRFDPRK SSTFRNLGKP LSIHYGTGSM EGFLGYDTVT
                      Pig  PSVYCKSDAC QNHHRFNPSK SSTFQNLDKP LSIQYGTGSI QGFLGYDTVM
                      Rat  PSVYCSSKVC RNHNRFDPSK SFTFQNLSKP LFVQYGTGSV EGFLAYDTVT 151                                                  200
     Bos_bovis_chymosin_B  VSNIVDIQQT VGLSTQEPGD VFTYAEFDGI LGMAYPSLAS EYSIPVFDNM
                    Sheep  VSNIVDIQQT VGLSTQEPGD VFTYAEFDGI LGMAYPSLAS EYSVPVFDNM
             C._bactrianus VSNIVDPNQT VGLSTEQPGE VFTYSEFDGI LGLAYPSLAS EYSVPVFDNM
        Camelus_dromedarius VSNIVDPNQT VGLSTEQPGE VFTYSEFDGI LGLAYPSLAS EYSVPVFDNM
                      Pig  VAGIVDAHQT VGLSTQEPSD IFTYSEFDGI LGLGYPELAS EYTVPVFDNM
                      Rat  VSDIVVPHQT VGLSTEEPGD IFTYSPFDGI LGLAYPTFAS KYSVPIFDNM 201                                                  250
     Bos_bovis_chymosin_B  MNRHLVAQDL FSVYMDRNGQ ESMLTLGAID PSYYTGSLHW VPVTVQQYWQ
                    Sheep  MDRRLVAQDL FSVYMDRSGQ GSMLTLGAID PSYYTGSLHW VPVTLQKYWQ
             C._bactrianus MDRHLVARDL FSVYMDRNGQ GSMLTLGATD PSYYTGSLHW VPVTVQQYWQ
        Camelus_dromedarius MDRHLVARDL FSVYMDRNGQ GSMLTLGAID PSYYTGSLHW VPVTLQQYWQ
                      Pig  MHRHLVAQDL FAVYMSRNDE GSMLTLGAID PSYYTGSLHW VPVTMQLYWQ
                      Rat  MNRHLVAQDL FSVYMSRNDQ GSMLTLGAID QSYFIGSLHW VPVTVQGYWQ 251                                                  300
     Bos_bovis_chymosin_B  FTVDSVTISG VVVACEGGCQ AILDTGTSKL VGPSSDILNI QQAIGATQNQ
                    Sheep  FTVDSVTISG AVVACEGGCQ AILDTGTSKL VGPSSDILNI QQAIGATQNQ
             C._bactrianus VTVDSVTING VAVACVGGCQ AILDTGTSVL FGPSSDILKI QMAIGATENR
        Camelus_dromedarius FTVDSVTING VAVACVGGCQ AILDTGTSVL FGPSSDILKI QMAIGATENR
                      Pig  FTVDSVTING VVVACNGGCQ AILDTGTSML AGPSSDILNI QMAIGATESQ
                      Rat  FTVDRITIND EVVACQGGCP AVLDTGTALL TGPGRDILNI QHAIGAVQGQ 301                                                  350
     Bos_bovis_chymosin_B  YGEFDIDCDN LSYMPTVVFE INGKMYPLTP SAYTSQDQGF CTSGFQSENH
                    Sheep  YGEFDIDCDS LSSMPTVVFE INGKMYPLTP YAYTSQEEGF CTSGFQGENH
             C._bactrianus YGEFDVNCGS LRSMPTVVFE INGRDFPLAP SAYTSKDQGF CTSGFQGDNN
        Camelus_dromedarius YGEFDVNCGN LRSMPTVVFE INGRDYPLSP SAYTSKDQGF CTSGFQGDNN
                      Pig  YGEFDIDCGS LSSMPTVVFE ISGRMYPLPP SAYTNQDQGF CTSGFQGDSK
                      Rat  HDQFDIDCWR LNFMPTVVFE INGREFPLPP SAYTNQFQGS CSSGFR..HG 351                   381
     Bos_bovis_chymosin_B  SQKWILGDVF IREYYSVFDR ANNLVGLAKA I
                    Sheep  SHQWILGDVF IREYYSVFDR ANNLVGLAKA I
             C._bactrianus SELWILGDVF IREYYSVFDR ANNRVGLAKA I
        Camelus_dromedarius SELWILGDVF IREYYSVFDR ANNRVGLAKA I
                      Pig  SQHWILGVVF IQEYYSVFDR ANNRVGLAKA I
                      Rat  SQMWILGDVF IREFYSVFDR ANNRVGLAKA I
```

VARIANTS OF CHYMOSIN WITH IMPROVED MILK-CLOTTING PROPERTIES

CROSS-REFERENCE TO RELATED APPLICATIONS

The present application is the U.S. National Stage of International Application PCT/EP2017/062086, filed May 19, 2017, and claims priority to European Patent Application No. 16170411.9, filed May 19, 2016.

SEQUENCE LISTING

The instant application contains a Sequence Listing, which has been filed electronically in ASCII format and is hereby incorporated by reference in its entirety. Said ASCII copy, created on April 15, 2020, is named P6080US00-030427-0285_SL.txt and is 31,281 bytes in size.

FIELD OF THE INVENTION

The present invention relates to variants of chymosin with improved milk-clotting properties.

BACKGROUND ART

Chymosin (EC 3.4.23.4) and pepsin (EC 3.4.23.1), the milk clotting enzymes of the mammalian stomach, are aspartic proteases belonging to a broad class of peptidases.

When produced in the gastric mucosal cells, chymosin and pepsin occur as enzymatically inactive pre-prochymosin and pre-pepsinogen, respectively. When chymosin is excreted, an N-terminal peptide fragment, the pre-fragment (signal peptide) is cleaved off to give prochymosin including a pro-fragment. Prochymosin is a substantially inactive form of the enzyme which, however, becomes activated under acidic conditions to the active chymosin by autocatalytic removal of the pro-fragment. This activation occurs in vivo in the gastric lumen under appropriate pH conditions or in vitro under acidic conditions.

The structural and functional characteristics of bovine, i.e. Bos taurus, pre-prochymosin, prochymosin and chymosin have been studied extensively. The pre-part of the bovine pre-prochymosin molecule comprises 16 aa residues and the pro-part of the corresponding prochymosin has a length of 42 aa residues. The active bovine chymosin comprises 323 aa.

Chymosin is produced naturally in mammalian species such as bovines, camels, caprines, buffaloes, sheep, pigs, humans, monkeys and rats.

Bovine and camel chymosin has for a number of years been commercially available to the dairy industry.

Enzymatic coagulation of milk by milk-clotting enzymes, such as chymosin and pepsin, is one of the most important processes in the manufacture of cheeses. Enzymatic milk coagulation is a two-phase process: a first phase where a proteolytic enzyme, chymosin or pepsin, attacks κ-casein, resulting in a metastable state of the casein micelle structure and a second phase, where the milk subsequently coagulates and forms a coagulum (reference 1).
WO02/36752A2 (Chr. Hansen) describes recombinant production of camel chymosin.
WO2013/174840A1 (Chr. Hansen) describes mutants/variants of bovine and camel chymosin.
WO2013/164479A2 (DSM) describes mutants of bovine chymosin.

The references listed immediately below may in the present context be seen as references describing mutants of chymosin:
Suzuki et al: Site directed mutagenesis reveals functional contribution of Thr218, Lys220 and Asp304 in chymosin, Protein Engineering, vol. 4, January 1990, pages 69-71;
Suzuki et al: Alteration of catalytic properties of chymosin by site-directed mutagenesis, Protein Engineering, vol. 2, May 1989, pages 563-569;
van den Brink et al: Increased production of chymosin by glycosylation, Journal of biotechnology, vol. 125, September 2006, pages 304-310;
Pitts et al: Expression and characterisation of chymosin pH optima mutants produced in Tricoderma reesei, Journal of biotechnology, vol. 28, March 1993, pages 69-83;
M.G. Williams et al: Mutagenesis, biochemical characterization and X-ray structural analysis of point mutants of bovine chymosin, Protein engineering design and selection, vol. 10, September 1997, pages 991-997;
Strop et al: Engineering enzyme subsite specificity: preparation, kinetic characterization, and x-ray analysis at 2.0 ANG resolution of Val111phe site mutated calf chymosin, Biochemistry, vol. 29, October 1990, pages 9863-9871;
Chitpinityol et al: Site-specific mutations of calf chymosin B which influence milk-clotting activity, Food Chemistry, vol. 62, June 1998, pages 133-139;
Zhang et al: Functional implications of disulfide bond, Cys45-Cys50, in recombinant prochymosin, Biochimica et biophysica acta, vol. 1343, December 1997, pages 278-286.

None of the prior art references mentioned above describe directly and unambiguously any of the chymosin variants with improved specific clotting activity or increased C/P ratios compared to the parent from which the variant is derived, as described below.

SUMMARY

The problem to be solved by the present invention is to provide variants of chymosin which when compared to the parent polypeptide, have either increased specific clotting activity or increased C/P ratio or both.

Based on intelligent design and comparative analyses of different variants, the present inventors identified a number of amino acid positions that are herein important in the sense that by making a variant in one or more of these positions in a parent peptide one may get an improved chymosin variant with either increased specific clotting activity or increased C/P ratios or both.

The amino acid numbering as used herein to specify the variant is based on the mature peptide. As known in the art—different natural wildtype chymosin polypeptide sequences obtained from different mammalian species (such as e.g. bovines, camels, sheep, pigs, or rats) are having a relatively high sequence similarity/identity. In FIG. 1 this is exemplified by an alignment of herein relevant different chymosin sequences.
In view of this relatively close sequence relationship—it is believed that the 3D structures of different natural wildtype chymosins are also relatively similar.

In the present context—a naturally obtained wildtype chymosin (such as bovine chymosin or camel chymosin) may herein be an example of a parent polypeptide—i.e. a parent polypeptide to which an alteration is made to produce a variant chymosin polypeptide of the present invention.

Without being limited to theory—it is believed that the herein discussed chymosin related amino acid positions are of general importance in any herein relevant chymosin enzyme of interest (e.g. chymosins of e.g. bovines, camels, sheep, pigs, rats etc.)—in the sense that by making a variant in one or more of these positions one may get an improved chymosin variant in general (e.g. an improved bovine, camel, sheep, pig or rat chymosin variant).

As discussed herein—as a reference sequence for determining the amino acid position of a parent chymosin polypeptide of interest (e.g. camel, sheep, bovine etc.) is herein used the public known *Camelius dromedarius* mature chymosin sequence of SEQ ID NO:2 herein. It may herein alternatively be termed camel chymosin. The sequence is also shown in FIG. 1 herein.

In the present context it is believed that a parent chymosin polypeptide (e.g. from sheep or rat) that has at least 80% sequence identity with the mature polypeptide of SEQ ID NO:2 (camel chymosin) may herein be seen as sufficient structural related to e.g. bovine or camel chymosin in order to be improved by making a variant in any of the amino acid positions as described herein.

Embodiments of the present invention are described below.

DEFINITIONS

All definitions of herein relevant terms are in accordance of what would be understood by the skilled person in relation to the herein relevant technical context.

The term "chymosin" relates to an enzyme of the EC 3.4.23.4 class. Chymosin has a high specificity and predominantly clots milk by cleavage of a single 104Ser-Phe-I-Met-Ala-107 bond in κ-chain of casein. As a side-activity, chymosin also cleaves α-casein primarily between Phe23 and Phe24 and β-casein primarily between Leu192 and Tyr193 (references 2, 3). The resulting peptides αS1(1-23) and β(193-209) will be further degraded by proteases from microbial cultures added to the ripening cheese (reference 4). An alternative name of chymosin used in the art is rennin.

The term "chymosin activity" relates to chymosin activity of a chymosin enzyme as understood by the skilled person in the present context.

The skilled person knows how to determine herein relevant chymosin activity.

As known in the art—the herein relevant so-called C/P ratio is determined by dividing the specific clotting activity (C) with the proteolytic activity (P). As known in the art—a higher C/P ratio implies generally that the loss of protein during e.g. cheese manufacturing due to non-specific protein degradation is reduced which may lead to cheese yield improvements.

The term "isolated variant" means a variant that is modified by the act of man. In one aspect, the variant is at least 1% pure, e.g., at least 5% pure, at least 10% pure, at least 20% pure, at least 40% pure, at least 60% pure, at least 80% pure, and at least 90% pure, as determined by SDS PAGE.

The term "mature polypeptide" means a peptide in its final form following translation and any post-translational modifications, such as N-terminal processing, C-terminal truncation, glycosylation, phosphorylation, etc. In the present context may a herein relevant mature chymosin polypeptide be seen as the active chymosin polypeptide sequence—i.e. without the pre-part and/or pro-part sequences. Herein relevant examples of a mature polypeptide are e.g. the mature polypeptide of SEQ ID NO:1 (bovine chymosin), which is from amino acid position 59 to amino acid position 381 of SEQ ID NO:1 or the mature polypeptide of SEQ ID NO:2 (camel chymosin), which is from amino acid position 59 to amino acid position 381 of SEQ ID NO:2.

The term "parent" or "parent polypeptide having chymosin activity" means a polypeptide to which an alteration is made to produce the enzyme variants of the present invention. The parent may be a naturally occurring (wild-type) polypeptide or a variant thereof.

The term "Sequence Identity" relates to the relatedness between two amino acid sequences or between two nucleotide sequences. For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the nobrief option) is used as the percent identity and is calculated as follows:

(Identical Residues—100)/(Length of Alignment—Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows: (Identical Deoxyribonucleotides× 100)/(Length of Alignment—Total Number of Gaps in Alignment).

The term "variant" means a peptide having chymosin activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The amino acid may be natural or unnatural amino acids—for instance, substitution with e.g. a particularly D-isomers (or D-forms) of e.g. D-alanine could theoretically be possible.

The term "wild-type" peptide refers to a nucleotide sequence or peptide sequence as it occurs in nature, i.e. nucleotide sequence or peptide sequence which hasn't been subject to targeted mutations by the act of man.

DRAWINGS

FIG. 1: An alignment of herein relevant different chymosin sequences. As understood by the skilled person in the present context—herein relevant sequence identity percentages of mature polypeptide sequences of e.g. sheep (SEQ ID NO: 10), C. bactrianus (SEQ ID NO: 9), camel (SEQ ID NO: 8), pig (SEQ ID NO: 7) or rat (SEQ ID NO: 6) chymosin with bovine chymosin (SEQ ID NO: 11), corresponding to the mature polypeptide of SEQ ID NO:3 (bovine chymosin—i.e. amino acid positions 59 to 381 of SEQ ID NO:3), are relatively similar to above mentioned sequence identity percentages.

FIG. 2: 3D structure of camel chymosin (detail, PDB: 4AA9) with a model of bound κ-casein shown in green. κ-casein is placed in the chymosin substrate binding cleft with the scissile bond between residues 105 and 106. Mutations R242E, Y243E, N249D, G251D, N252D, R254E, S273D, Q280E, F282E are highlighted in blue.

Figure 3:
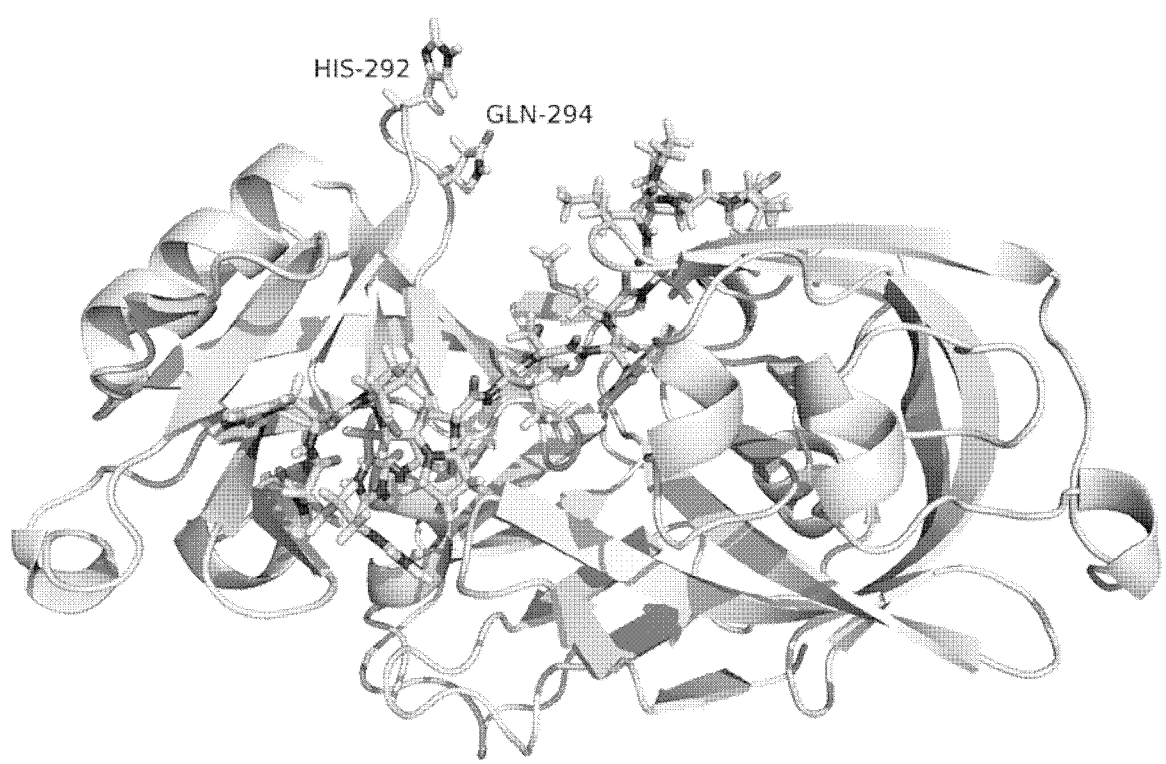

FIG. 3: 3D structure of bovine chymosin (PDB: 4AA8) with a model of bound κ-casein shown in green. κ-casein is placed in the chymosin substrate binding cleft with the scissile bond between residues 105 and 106. Positions H292 and Q294 are highlighted in yellow.

Figure 4:
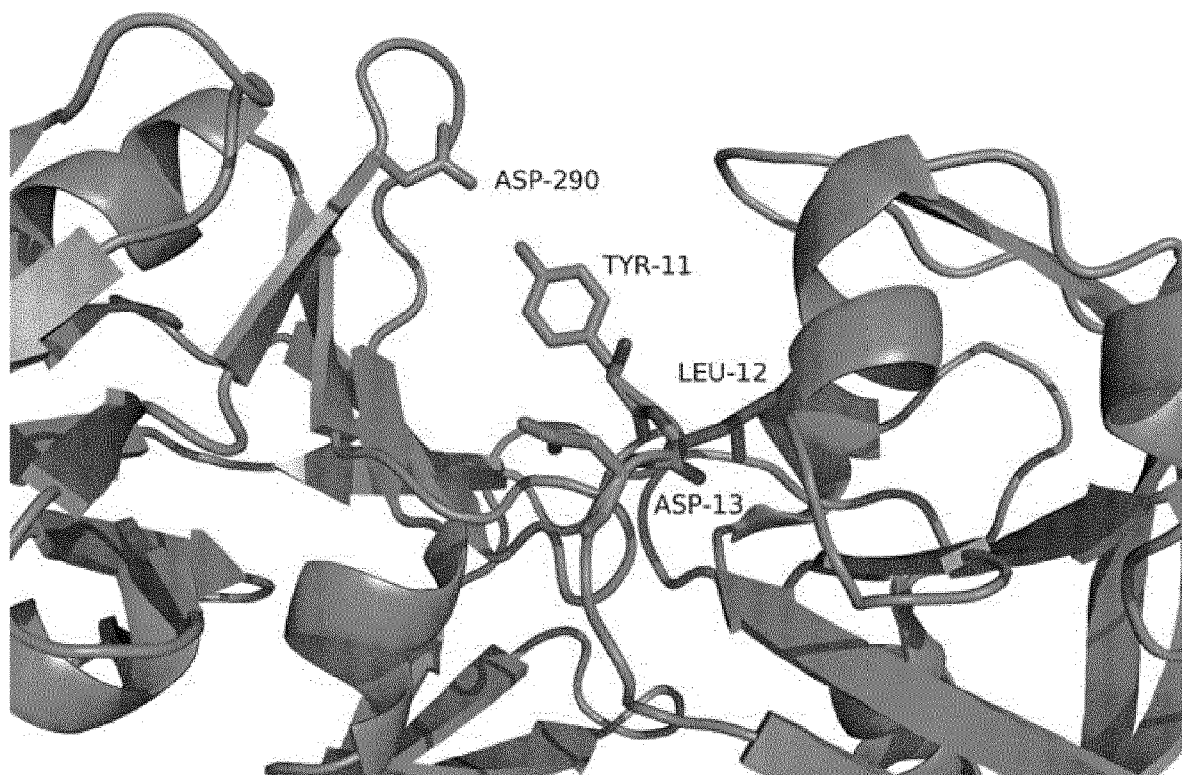

FIG. 4: 3D structure of camel chymosin (detail, PDB: 4AA9). Residues Y11, L12, and D13 of the protein N-terminus as well as the potential Y11 interaction partner D290 are highlighted in purple.

DETAILED DESCRIPTION OF THE INVENTION

Determining the Amino Acid Position of a Chymosin of Interest

As discussed above—as a reference sequence for determining the amino acid position of a herein relevant chymosin polypeptide of interest (e.g. camel, sheep, bovine etc.) is herein used the public known camel chymosin sequence disclosed as SEQ ID NO:2 herein.

The amino acid sequence of another chymosin polypeptide is aligned with the polypeptide disclosed in SEQ ID NO:2, and based on the alignment, the amino acid position number corresponding to any amino acid residue in the polypeptide disclosed in SEQ ID NO:2 is determined using the ClustalW algorithm as described in working Example 1 herein.

Based on above well-known computer programs—it is routine work for the skilled person to determine the amino acid position of a herein relevant chymosin polypeptide of interest (e.g. camel, sheep, bovine etc.).

In FIG. 1 herein is shown an example of an alignment. Just as an example—in FIG. 1 can e.g. be seen that herein used bovine reference SEQ ID NO:3 has a "G" in position 50 and "*Camelus_dromedarius*" (SEQ ID NO:2 herein) has an "A" in this position 50.

Nomenclature of Variants

In describing the variants of the present invention, the nomenclature described below is adapted for ease of reference. The accepted IUPAC single letter or three letter amino acid abbreviations are employed.

The specific variants discussed in this "nomenclature" section below may not be herein relevant variants of the present invention—i.e. this "nomenclature" section is just to describe the herein relevant used nomenclature as such.

Substitutions. For an amino acid substitution, the following nomenclature is used: Original amino acid, position, substituted amino acid. Accordingly, a theoretical substitution of threonine with alanine at position 226 is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. A substitution e.g. designated "226A" refers to a substitution of a parent amino acid (e.g. T, Q, S or another parent amino acid) with alanine at position 226.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195* +S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple alterations. Variants comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different substitutions. Where different substitutions can be introduced at a position, the different substitutions are separated by a comma, e.g., "Arg170Tyr,Glu" or "R170Y,E" represents a substitution of arginine with tyrosine or glutamic acid at position 170. Thus, "Tyr167Gly,Ala+Arg170Gly,Ala" or "Y167G,A+R170G,A" designates the following variants: "Tyr167Gly+Arg170Gly", "Tyr167Gly+Arg170Ala", "Tyr167Ala+Arg170Gly", and "Tyr167Ala+Arg170Ala".

Preferred parent polypeptide having chymosin activity Preferably, the parent polypeptide has at least 80%, 85%, 90%, 95%, 97%, 98%, 99% or 100% sequence identity with the mature polypeptide of SEQ ID NO:3 (bovine chymosin) and/or SEQ ID NO:2 (camel chymosin).

Just as an example—a herein suitable relevant parent polypeptide could e.g. be bovine chymosin A—as known in the art bovine chymosin A may only have one amino acid difference as compared to bovine chymosin B of SEQ ID NO:3 herein.

In a preferred embodiment—the parent polypeptide has at least 90% sequence identity with the mature polypeptide of SEQ ID NO:3 (bovine chymosin), more preferably the parent polypeptide has at least 95% sequence identity with the mature polypeptide of SEQ ID NO:3 (bovine chymosin) and even more preferably the parent polypeptide has at least 97% sequence identity with the mature polypeptide of SEQ ID NO:3 (bovine chymosin). It may be preferred that the parent polypeptide is the mature polypeptide of SEQ ID NO:3 (bovine chymosin).

As understood by the skilled person in the present context—a herein relevant parent polypeptide having chymosin activity may already e.g. be a variant of e.g. a corresponding wildtype chymosin.

For instance, a bovine chymosin variant with e.g. 5-10 alterations (e.g. substitutions) as compared to mature wildtype bovine chymosin polypeptide of SEQ ID NO:3 may still be a parent polypeptide that has at least 95% sequence identity with the mature polypeptide of SEQ ID NO:3 (Bovine chymosin).

Said in other words and in general—a herein relevant isolated chymosin polypeptide variant may comprise alterations (e.g. substitutions) in other positions than the positions claimed herein.

As understood by the skilled person in the present context—a parent polypeptide may be a polypeptide that has at least 80% sequence identity with the mature polypeptide of SEQ ID NO:2 (Camel). In a preferred embodiment—the parent polypeptide has at least 92% sequence identity with the mature polypeptide of SEQ ID NO:2 and/or SEQ ID NO:3, more preferably the parent polypeptide has at least 95% sequence identity with the mature polypeptide of SEQ ID NO:2 and/or SEQ ID NO:3 and even more preferably the parent polypeptide has at least 97% sequence identity with the mature polypeptide of SEQ ID NO:2 or SEQ ID NO:3. It may be preferred that the parent polypeptide is the mature polypeptide of SEQ ID NO:2 (camel chymosin).

As understood by the skilled person in the present context—an isolated chymosin variant may comprise alterations (e.g. substitutions) in other amino acid positions than given above.

For instance, a bovine chymosin variant with e.g. 5-10 alterations (e.g. substitutions) as compared to wildtype camel chymosin polypeptide of SEQ ID NO:2 will still be a parent polypeptide that has at least 95% sequence identity with the mature polypeptide of SEQ ID NO:2.

It may be preferred that the isolated bovine chymosin variant comprises less than 30 amino acid alterations (e.g. substitutions) as compared to the mature polypeptide of SEQ ID NO:2 (camel chymosin) or it may be preferred that the isolated camel chymosin variant comprises less than 20 amino acid alterations (e.g. substitutions) as compared to the mature polypeptide of SEQ ID NO:2 or it may be preferred that the isolated bovine chymosin variant comprises less than 10 amino acid alterations (e.g. substitutions) as compared to the mature polypeptide of SEQ ID NO:2 or it may be preferred that the isolated camel chymosin variant comprises less than 5 amino acid alterations (e.g. substitutions) as compared to the mature polypeptide of SEQ ID NO:2 (camel chymosin).

Method for Making Isolated Chymosin Polypeptide Variants

As discussed above—as known in the art, the skilled person may, based on his common general knowledge, routinely produce and purify chymosin and chymosin variants.

Said in other words, once the skilled person is in possession of a herein relevant parent polypeptide having chymosin activity of interest (e.g. from bovines, camels, sheep, pigs, or rats) it is routine work for the skilled person to make a variant of such a parent chymosin of interest when guided by present disclosure.

An example of a suitable method to produce and isolate a chymosin (variant or parent) may be by well-known e.g. fungal recombinant expression/production based technology as e.g. described in WO02/36752A2 (Chr. Hansen).

It is also routine work for the skilled person to make alteration at one or more positions in a parent polypeptide having chymosin activity, wherein the alteration is comprising a substitution, a deletion or an insertion in at least one amino acid position as disclosed herein.

As known to the skilled person—this may e.g. be done by so-called site directed mutagenesis and recombinant expression/production based technology.

It is also routine work for the skilled person to determine if a herein relevant parent polypeptide (e.g. camel or bovine wildtype chymosin) and/or a herein relevant variant has chymosin activity or not.

As known in the art—chymosin specificity may be determined by the so-called C/P ratio, which is determined by dividing the specific clotting activity (C) with the proteolytic activity (P). As known in the art—a higher C/P ratio implies generally that the loss of protein during e.g. cheese manufacturing due to nonspecific protein degradation is reduced, i.e. the yield of cheese is improved.

Determination of Milk Clotting Activity

Milk clotting activity may be determined using the REMCAT method, which is the standard method developed by the International Dairy Federation (IDF method). Milk clotting activity is determined from the time needed for a visible flocculation of a standard milk substrate prepared from a low-heat, low fat milk powder with a calcium chloride solution of 0.5 g per liter (pH≈6.5). The clotting time of a rennet sample is compared to that of a reference standard having known milk-clotting activity and having the same enzyme composition by IDF Standard 110B as the sample. Samples and reference standards are measured under identical chemical and physical conditions. Variant samples are adjusted to approximately 3 IMCU/ml using an 84 mM acetic acid buffer pH 5.5. Hereafter, 20 µl enzyme preparation is added to 1 ml preheated milk (32° C.) in a glass test tube placed in a water bath, capable of maintaining a constant temperature of 32° C.±1° C. under constant stirring. The total milk-clotting activity (strength) of a rennet is calculated in International Milk-Clotting Units (IMCU) per ml relative to a standard having the same enzyme composition as the sample according to the formula:

$$\text{Strength in } IMCU/\text{ml} = \frac{Sstandard \times Tstandard \times Dsample}{Dstandard \times Tsample}$$

Sstandard: The milk-clotting activity of the international reference standard for rennet.
Tstandard: Clotting time in seconds obtained for the standard dilution. Dsample: Dilution factor for the sample
Dstandard: Dilution factor for the standard
Tsample: Clotting time in seconds obtained for the diluted rennet sample from addition of enzyme to time of flocculation.

For clotting activity determination the µIMCU method may be used instead of the REMCAT method. As compared to REMCAT, flocculation time of chymosin variants in the µIMCU assay is determined by OD measurements in 96-well microtiter plates at 800 nm in a UV/VIS plate reader. A standard curve of various dilutions of a reference standard with known clotting strength is recorded on each plate. Samples are prepared by diluting enzyme in 84 mM acetate buffer, 0.1% triton X-100, pH 5.5. Reaction at 32° C. is started by adding 250 uL of a standard milk substrate containing 4% (w/w) low-heat, low fat milk powder and 7.5% (w/w) calcium chloride (pH≈6.5) to 25 uL enzyme sample. Milk clotting activity of chymosin variants in International Milk-Clotting Units (IMCU) per ml is determined based on sample flocculation time relative to the standard curve.

Determination of Total Protein Content

Total protein content may preferably be determined using the Pierce BCA Protein Assay Kit from Thermo Scientific following the instructions of the providers.

Calculation of Specific Clotting Activity

Specific clotting activity (IMCU/mg total protein) was determined by dividing the clotting activity (IMCU/ml) by the total protein content (mg total protein per ml).

Determination of Proteolytic Activity

General proteolytic activity may preferably be measured using fluorescently labelled Bodipy-FL casein as a substrate (EnzChek; Molecular Bioprobes, E6638). Casein derivatives heavily labeled with pH-insensitive green-fluorescent Bodipy-FL result in quenching of the conjugate's fluorescence. Protease catalyzed hydrolysis releases fluorescent Bodipy-FL. This method is very sensitive which was essential for this experiment as the reference has the lowest general proteolytical activity of all coagulants known to date. A 0.04 mg/ml substrate solution is prepared in 0.2 M phosphate buffer pH 6.5, containing 100 mM NaCl, 5% glycerol, and 0.1% Brij. Chymosin variants are dissolved in 20 mM malonate buffer, containing 100 mM NaCl, 5% glycerol, and 0.1% Brij. Of both reference and chymosin variant solutions, 20 μl are mixed in a black 384-well Corning flat bottom polystyrene microtiter plate and fluorescence was continuously recorded in a fluorometer at 32 C for 10 hours. Slopes of the linear part of fluorescence change are used to determine general proteolytic activity.

Determination of the C/P Ratio

The C/P ratio is calculated by dividing the clotting activity (C) with the proteolytic activity (P).

Statistical Analysis of the Positional and Mutational Effects on Specific Clotting Activity and C/P Ratio A statistical machine-learning approach and PCA-based analysis may preferably be used to determine the effects of single mutations present in the multi-substitution variants, i.e. specific milk clotting activity, as well as on the ratio of clotting and general proteolytic activity (C/P).

Preferred Embodiments of the Invention

As outlined above and illustrated in the examples below, the inventors of present disclosure have made a number of preferred chymosin polypeptide variants with improved clotting activity and/or C/P ratio when compared to the corresponding parent polypeptide under comparable conditions.

In a preferred aspect, the present invention relates to an isolated chymosin polypeptide variant comprising an alteration in one or more positions compared to a parent polypeptide having chymosin activity, wherein the alteration comprise a substitution, a deletion or an insertion in at least one amino acid position corresponding to any of positions: D59, V309, S132, N249, L166, N249, Q56, Y134, K295, M157, M256, R242, I96, H76, S164, S273, G251, Y11, L166, K19, Y21,
S74, Y243, N249, S273, Q280, F282, L295, N252, R254, G70, V136, L222, K231, N291.
wherein
(i): the amino acid position of the parent polypeptide is determined by an alignment of the parent polypeptide with the polypeptide of SEQ ID NO:2 and
(ii): the parent polypeptide has at least 80% sequence identity with the mature polypeptide of SEQ ID NO:2 (camel chymosin);
wherein the isolated chymosin polypeptide variant has a higher specific clotting activity and/or C/P ratio than its corresponding parent polypeptide.

More specifically, the isolated chymosin polypeptide variant of present invention has a specific clotting activity (IMCU/mg total protein) that is at least 85% such as e.g. at least 90%, 100%, 110%, 120%, 130%, 160% or 200% of the specific clotting activity of its parent polypeptide. Alternatively or additionally, the isolated chymosin polypeptide variant of present invention has a C/P ratio that is at least 200%, such as e.g. at least 400%, at least 500%, at least 750% or at least 1000% of the C/P ratio of its parent polypeptide.

As specified above, the parent polypeptide may have at least 80%, such as at least e.g. 82%, 85%, 95%, 97%, 98%, 99% or 100% sequence identity with the mature polypeptide of SEQ ID NO:2 (camel chymosin).

The alteration may comprise a substitution selected from a list consisting of:
D59N, V309I, S132A, N249E, L166V, N249D, Q56H, Y134G, K295L, M157L, M256L, R242E, I96L, H76Q, S164G, S273Y, G251D, Y11I, R242D, L222V, Y11V, L166I, K19T, Y21S, S74D, Y243E, N249D, S273D, Q280E, F282E, L295K, N252D, R254E, G70D, V136I, L222I, K231N, N291Q.

In a related embodiment, the present invention relates to an isolated chymosin polypeptide variant wherein the alteration comprises one or more combinations of substitutions comprising:
Y11V, K19T, D59N, I96L, S164G, L166V, L222V, R242E, N249E, L253I;
Y11I, D59N, I96L, S164G, L166V, L222V, R242E, G251D, L253I;
Y11I, I96L, S164G, L222I, R242E;
Y11I, K19T, D59N, I96L, S164G, L222I, R242E, N249E, G251D;
H76Q, I96L, S164G, L222I, R242E, G251D, S273Y;
K19T, D59N, H76Q, S164G, L222I, N249D, S273Y;
K19T, D59N, H76Q, L166V, L222I, R242E, G251D, S273Y;
K19T, D59N, H76Q, S132A, L222I, G251D, S273Y, V309I;
Y21S, H76Q, S164G, L222I, R242E, G251D, S273Y;
D59N, S132A, S164G, L222I, R242E, N249D, G251D, S273Y;
D59N, H76Q, I96L, S132A, S164G, L166V, L222I, G251D, S273Y;
H76Q, S164G, L166V, L222I, R242E, G251D, S273Y;
D59N, H76Q, S132A, S164G, L166V, S273Y;
K19T, D59N, H76Q, S164G, R242E, N249D, G251D, S273Y;
Y21S, D59N, H76Q, I96L, S164G, L222I, N249D, G251D, S273Y;
K19T, D59N, I96L, S164G, L222I, G251D;
D59N, H76Q, S164G, L222I, S226T, R242E;
H76Q, L130I, L222I, S226T, G251D, S273Y;

Y21S, D59N, H76Q, I96L, L222I, S273Y;
H76Q, S164G, L222I, N249D, G251D, S273Y, V309I;
D59N, I96L, L166V, L222I, R242E, G251D;
Y11V, K19T, D59N, I96L, S164G, L166V, L222I, R242E, G251D, L253I;
K19S, D59N, I96L, S164G, L222I, R242E, N249E, G251D;
K19T, D59N, I96L, S164G, L166I, L222I, R242E, N249D;
H76Q, I96L, S164G, L222I, R242E, G251D, S273Y;
K19T, I96L, L222I, R242E, L253I;
K19T, D59N, I96L, S164G, L222V, R242E, N249D, L253I;
I96L, S164G, L222I, R242E, G251D, S274Y;
R242E, N252D, N100Q, N291Q;
R242E, R254E, Q280E, N100Q, N291Q;
R242E, Q280E, N100Q, N291Q;
R242E, R254E, S273D, Q280E, N100Q, N291Q;
R67Q, S132A, L222I, K231N, R242E, V248I;
R67Q, I96L, L130I, M157L, K231N, R242E;
R67Q, M157L, L222I, K231N, V248I;
R67Q, I96L, M157L, L222I, K231N or
R67Q, G70D, M157L, L222I, N291Q;

Optionally, the isolated chymosin polypeptide variant may further comprise substitutions that alter the glycosylation pattern, such as e.g. substitutions in one or more of positions N100, N252 and/or N291, more specifically N100Q, N252Q and/or N291Q.

Preferred Methods for Making Isolated Chymosin Polypeptide Variants

The present invention further relates to methods for producing an isolated polypeptide according to present disclosure.

As a related embodiment, the present invention relates to a method for making an isolated chymosin polypeptide variant wherein the method comprises the steps:

(a): making an alteration at one or more positions in a parent polypeptide, wherein the alteration is comprising a substitution, a deletion or an insertion in at least one amino acid position corresponding to any of positions: D59, V309, S132, N249, L166, N249, Q56, Y134, K295, M157, M256, R242, I96, H76, S164, S273, G251, Y11, L166, K19, Y21, S74, Y243, N249, S273, Q280, F282, L295, N252, R254, G70, V136, L222, K231, N291, (b): producing and isolating the altered polypeptide of step (a), and wherein:

(i): the amino acid position of the parent polypeptide is determined by an alignment of the parent polypeptide with the polypeptide of SEQ ID NO:2 (camel chymosin); and (ii): the parent polypeptide has at least 80% sequence identity with the mature polypeptide of SEQ ID NO:3 (bovine chymosin) and/or at least 80% sequence identity with the mature polypeptide of SEQ ID NO:2 (camel chymosin).

More specifically, the alteration may be one or more of the substitutions: D59N, V309I, S132A, N249E, L166V, N249D, Q56H, Y134G, K295L, M157L, M256L, R242E, I96L, H76Q, S164G, S273Y, G251D, Y11I, R242D, L222V, Y11V, L166I, K19T, Y21S, S74D, Y243E, N249D, S273D, Q280E, F282E, L295K, N252D, R254E, G70D, V136I, L222I, K231N, N291Q.

In yet a related aspect, the present invention relates to a method for making an isolated chymosin polypeptide variant as specified above, wherein the isolated chymosin polypeptide variant comprises substitution in one or more of the combinations of positions comprising the positions corresponding to:

Y11V, K19T, D59N, I96L, S164G, L166V, L222V, R242E, N249E, L253I;
Y11I, D59N, I96L, S164G, L166V, L222V, R242E, G251D, L253I;
Y11I, I96L, S164G, L222I, R242E;
Y11I, K19T, D59N, I96L, S164G, L222I, R242E, N249E, G251D;
H76Q, I96L, S164G, L222I, R242E, G251D, S273Y;
K19T, D59N, H76Q, S164G, L222I, N249D, S273Y;
K19T, D59N, H76Q, L166V, L222I, R242E, G251D, S273Y;
K19T, D59N, H76Q, S132A, L222I, G251D, S273Y, V309I;
Y21S, H76Q, S164G, L222I, R242E, G251D, S273Y;
D59N, S132A, S164G, L222I, R242E, N249D, G251D, S273Y;
D59N, H76Q, I96L, S132A, S164G, L166V, L222I, G251D, S273Y;
H76Q, S164G, L166V, L222I, R242E, G251D, S273Y;
D59N, H76Q, S132A, S164G, L166V, S273Y;
K19T, D59N, H76Q, S164G, R242E, N249D, G251D, S273Y;
Y21S, D59N, H76Q, I96L, S164G, L222I, N249D, G251D, S273Y;
K19T, D59N, I96L, S164G, L222I, G251D;
D59N, H76Q, S164G, L222I, S226T, R242E;
H76Q, L130I, L222I, S226T, G251D, S273Y;
Y21S, D59N, H76Q, I96L, L222I, S273Y;
H76Q, S164G, L222I, N249D, G251D, S273Y, V309I;
D59N, I96L, L166V, L222I, R242E, G251D;
Y11V, K19T, D59N, I96L, S164G, L166V, L222I, R242E, G251D, L253I;
K19S, D59N, I96L, S164G, L222I, R242E, N249E, G251D;
K19T, D59N, I96L, S164G, L166I, L222I, R242E, N249D;
H76Q, I96L, S164G, L222I, R242E, G251D, S273Y;
K19T, I96L, L222I, R242E, L253I;
K19T, D59N, I96L, S164G, L222V, R242E, N249D, L253I;
I96L, S164G, L222I, R242E, G251D, S274Y;
R242E, N252D, N100Q, N291Q;
R242E, R254E, Q280E, N100Q, N291Q;
R242E, Q280E, N100Q, N291Q;
R242E, R254E, S273D, Q280E, N100Q, N291Q;
R67Q, S132A, L222I, K231N, R242E, V248I;
R67Q, I96L, L130I, M157L, K231N, R242E;
R67Q, M157L, L222I, K231N, V248I;
R67Q, I96L, M157L, L222I, K231N or
R67Q, G70D, M157L, L222I, N291Q.

The parent polypeptide may as a preferred embodiment have at least 95% sequence identity with the mature polypeptide of SEQ ID NO:2 (Camel chymosin).

Further the present invention relates to method for making a food or feed product comprising adding an effective amount of the isolated chymosin polypeptide variant as described herein to the food or feed ingredient(s) and carrying our further manufacturing steps to obtain the food or feed product.

A further related aspect of present invention concerns a method for making a food or feed product comprising adding an effective amount of the isolated chymosin polypeptide variant as described herein to the food or feed ingredient(s) and carrying our further manufacturing steps to obtain the food or feed product, in particular wherein the food or feed product is a milk-based product or a food or feed product comprising a chymosin polypetide of present invention.

A further related aspect of present invention relates to a chymosin polypetide variant according to present invention in a process for making a milk based product such as e.g.

cheese, such as e.g. pasta filata, cheddar, continental type cheeses, soft cheese or white brine cheese.

As discussed above—an isolated chymosin polypeptide variant as described herein may be used according to the art—e.g. to make a milk based product of interest (such as e.g. a cheese product).

As discussed above—an aspect of the invention relates to a method for making a food or feed product comprising adding an effective amount of the isolated chymosin polypeptide variant as described herein to the food or feed ingredient(s) and carrying our further manufacturing steps to obtain the food or feed product.

Preferably, the food or feed product is a milk-based product and wherein the method comprises adding an effective amount of the isolated chymosin polypeptide variant as described herein to milk and carrying our further manufacturing steps to obtain the milk based product.

The milk may e.g. be soy milk, sheep milk, goat milk, buffalo milk, yak milk, lama milk, camel milk or cow milk.

The milk based product may e.g. be a fermented milk product such as a quark or a cheese.

As known in the art, the growth, purification, testing and general handling may influence the performance of enzymes and hence also the enzyme of present invention. Hence the present invention relates to chymosin polypeptide variants, methods for making these and products containing these, wherein the chymosin polypeptide variant has an improved clotting activity and/or C/P ratio when compared to the corresponding parent polypeptide under comparable conditions and preferably after being produced and otherwise handled under comparable conditions.

EXAMPLES

Example 1: Alignment and Numbering of Chymosin Protein Sequences and Variant Sequences Chymosin protein sequences were aligned using the ClustalW algorithm as provided by the EBI (EBI, tools, multiple sequence alignment, CLUSTALW", http://www.ebi.ac.uk/Tools/msa/clustalw2/) and as described in Larkin MA, Blackshields G, Brown NP, Chenna R, McGettigan PA, McWilliam H, Valentin F, Wallace IM, Wilm A, Lopez R, Thompson JD, Gibson TJ, Higgins DG (2007). Bioinformatics 23(21), 2947-2948.

ClustalW2 settings for multiple sequence alignments were Protein weight Matrix=BLOSUM, GAP open=10, GAP EXTENSION=0.5, GAP DISTANCES=8, No End Gaps, ITERATION=none, NUMITER=1, CLUSTERING=NJ As a reference sequence the bovine chymosin B prepro-chymosin was used (Genbank accession number P00794—disclosed herein as SEQ ID NO:1), where the N-terminal Methionin has number 1 (MRCL . . . ) and the C-terminal Isoleucin (in the protein sequence . . . LAKAI) has number 381. Variants were aligned against the bovine B pre-pro-chymosin and residues were numbered according to the corresponding bovine chymosin residue.

Example 2: Design of Chymosin Variants

Chymosin variants were designed using different strategies.

When there is referred to camel chymosin there is referred to camel chymosin comprising the polypeptide of SEQ ID NO:2 herein. Camel chymosin of SEQ ID NO:2 may be seen as a herein relevant parent polypeptide having chymosin activity used to make camel chymosin variants thereof.

When there is referred to bovine chymosin there is referred to bovine chymosin comprising the polypeptide of SEQ ID NO:1 herein. Bovine chymosin of SEQ ID NO:1 may be seen as a relevant parent polypeptide having chymosin activity used to make bovine chymosin variants thereof.

Variants 180 to 269 and 367 to 461 of camel chymosin were designed based on an alignment of a large set of public known aspartic protease sequences having an identity of 25% or more compared to bovine chymosin B. Variations were generally introduced in regions with a high level of amino acid variation between species, while conserved regions were not changed. Amino acid substitutions were chosen based on phylogenetic, structural and experimental information to identify changes with high probability to show beneficial effects on specific clotting activity and the C/P ratio. Multiple variations were introduced in each variant construct, ensuring that each single mutation was present in multiple variant constructs to minimize the effect of covariation between various substitutions. Machine learning and statistical analysis of experimental data were used to determine the relative contributions of the amino acid substitutions to measured coagulant performance of the chymosin variants (references 14, 15).

Variants 271 to 366 were designed based on detailed structural analysis of bovine chymosin (PDB code: 4AA8) and camel chymosin (PDB code: 4AA9). Variations were chosen based on the chemical nature of the respective amino acid side chains and their expected impact on either casein substrate binding or general enzyme properties. Most of the amino acid substitutions in variants 271 to 346 were made in sequence positions either within or in close structural proximity to the substrate binding cleft, or in secondary structural elements that get into contact with the bound casein substrate. Furthermore, changes were made in positions on the protein surface that alter the charge profile of these regions (reference 5) and are therefore expected to have an impact on enzyme performance. Variants 347 to 366 were made based on the different structural conformation of the N-terminal sequence in bovine and camel chymosin. Amino acid substitutions were made in positions within the substrate binding cleft that interact with the N-terminus in camel chymosin.

Example 3: Preparation of Chymosin Variant Enzyme Material

All chymosin variants were synthesized as synthetic genes and cloned into a fungal expression vector such as e.g. pGAMpR-C (described in WO02/36752A2)

The vectors were transformed into *E. coli* and plasmid DNA was purified using standard molecular biology protocols, known to the person skilled in the art. The variant plasmids were individually transformed into an *Aspergillus niger* or *Aspergillus nidulans* strain and protein was produced essentially as described in WO02/36752A2 and purified using standard chromatography techniques. For enzyme library screening, all chymosin variants were produced in 20-60 mL fermentations. For more detailed characterization of variants 433, 436, 453, and 457, the respective enzymes were fermented again in 70 L scale.

As known in the art—the skilled person may, based on his common general knowledge, produce and purify chymosin and chymosin variants—such as herein described bovine and camel chymosin variants.

Example 4: Determination of Specific Chymosin Activity 4.1 Determination of Milk Clotting Activity Milk clotting activity was determined using the REMCAT method, which is the standard method developed by the International Dairy Federation (IDF method). Milk clotting activity is determined from the time needed for a visible flocculation of a standard milk substrate prepared from a low-heat, low fat milk powder with a calcium chloride solution of 0.5 g per liter (pH≈6.5). The clotting time of a rennet sample is compared to that of a reference standard having known milkclotting activity and having the same enzyme composition by IDF Standard 110B as the sample. Samples and reference standards were measured under identical chemical and physical conditions. Variant samples were adjusted to approximately 3 IMCU/ml using an 84 mM acetic acid buffer pH 5.5. Hereafter, 20 µl enzyme preparation was added to 1 ml preheated milk (32° C.) in a glass test tube placed in a water bath, capable of maintaining a constant temperature of 32° C.±1° C. under constant stirring. The total milk-clotting activity (strength) of a rennet was calculated in International Milk-Clotting Units (IMCU) per ml relative to a standard having the same enzyme composition as the sample according to the formula:

$$\text{Strength in } IMCU/\text{ml} = \frac{S{standard} \times T{standard} \times D{sample}}{D{standard} \times T{sample}}$$

Sstandard: The milk-clotting activity of the international reference standard for rennet.

Tstandard: Clotting time in seconds obtained for the standard dilution.

Dsample: Dilution factor for the sample

Dstandard: Dilution factor for the standard

Tsample: Clotting time in seconds obtained for the diluted rennet sample from addition of enzyme to time of flocculation.

For clotting activity determination of libraries 1 and 3 variants as well as variants by structural design, the µIMCU method was used instead of the REMCAT method. As compared to REMCAT, flocculation time of chymosin variants in the µIMCU assay was determined by OD measurements in 96-well microtiter plates at 800 nm in a UV/VIS plate reader. A standard curve of various dilutions of a reference standard with known clotting strength was recorded on each plate. Samples were prepared by diluting enzyme in 84 mM acetate buffer, 0.1% triton X-100, pH 5.5. Reaction at 32° C. was started by adding 250 uL of a standard milk substrate containing 4% (w/w) low-heat, low fat milk powder and 7.5% (w/w) calcium chloride (pH≈6.5) to 25 uL enzyme sample. Milk clotting activity of chymosin variants in International Milk-Clotting Units (IMCU) per ml was determined based on sample flocculation time relative to the standard curve.

4.2 Determination of Total Protein Content

Total protein content was determined using the Pierce BCA Protein Assay Kit from Thermo Scientific following the instructions of the providers.

4.3 Calculation of Specific Clotting Activity

Specific clotting activity (IMCU/mg total protein) was determined by dividing the clotting activity (IMCU/ml) by the total protein content (mg total protein per ml).

Example 5 Determination of proteolytic activity

General proteolytic activity was measured using fluorescently labelled Bodipy-FL casein as a substrate (EnzChek; Molecular Bioprobes, E6638). Casein derivatives heavily labeled with pH-insensitive green-fluorescent Bodipy-FL result in quenching of the conjugate's fluorescence. Protease catalyzed hydrolysis releases fluorescent Bodipy-FL. This method is very sensitive which was essential for this experiment as CHYMAX M has the lowest general proteolytical activity of all coagulants known to date.

A 0.04 mg/ml substrate solution was prepared in 0.2 M phosphate buffer pH 6.5, containing 100 mM NaCl, 5% glycerol, and 0.1% Brij. Chymosin variants were solved in 20 mM malonate buffer, containing 100 mM NaCl, 5% glycerol, and 0.1% Brij. Of both substrate and chymosin variant solutions, 20µl were mixed in a black 384-well Corning flat bottom polystyrene microtiter plate and fluorescence was continuously recorded in a fluorometer at 32° C. for 10 hours. Slopes of the linear part of fluorescence change were used to determine general proteolytic activity.

Example 6 Statistical Analysis of the Positional and Mutational Effects on Specific Clotting Activity and C/P Ratio A statistical machine-learning approach and PCA-based analysis was used to determine the effects of all single mutations present in the variants of multisubstitution libraries 1 to 3 on cleavage of κ-casein between positions Phe105 and Met106, i.e. specific milk clotting activity, as well as on the ratio of clotting and general proteolytic activity (C/P).

Results

Multi-Substitution Library 1

Variants of camel chymosin, each having multiple substitutions compared to wild type, were generated and analyzed as described above. All variants have an amino acid sequence identical to camel chymosin (SEQ ID NO:2), except for the variations mentioned in the table. Camel chymosin (CHY-MAX M) is included as reference.

Clotting activities were determined using the µIMCU method.

TABLE 1

Enzymatic activities of camel chymosin variants 180-222. Numbers are given in % cleavage of wild type camel chymosin (CHY-MAX M).

| variant CHY-MAX M | mutations | | | | | | | | | Clotting (C) 100 | Proteolytic (P) 100 | C/P 100 |
|---|---|---|---|---|---|---|---|---|---|---|---|---|
| 180 | H76Q | S132A | S164G | L222I | N249D | G251D | | | | 72 | 37 | 194 |
| 181 | Y21S | D59N | H76Q | S164G | L166V | N249D | G251D | S273Y | | 77 | 37 | 210 |
| 182 | D59N | H76Q | S164G | L222I | R242E | S273Y | V309I | | | 96 | 21 | 449 |
| 183 | D59N | H76Q | L130I | L166V | L222I | N249D | G251D | S273Y | | 84 | 55 | 152 |
| 184 | Y21S | D59N | S164G | L222I | R242E | G251D | S273Y | V309I | | 102 | 35 | 287 |
| 185 | K19T | Y21S | D59N | H76Q | S132A | S164G | L222I | G251D | S273Y | 97 | 29 | 334 |
| 186 | D59N | H76Q | I96L | L130I | S164G | L222I | R242E | G251D | | 85 | 16 | 524 |
| 187 | H76Q | S164G | L166V | L222I | S226T | S273Y | | | | 103 | 21 | 504 |
| 188 | K19T | D59N | I96L | S164G | L222I | G251D | | | | 126 | 31 | 403 |
| 189 | Y21S | H76Q | S164G | L222I | R242E | G251D | S273Y | | | 138 | 14 | 975 |
| 190 | H76Q | I96L | S164G | L222I | R242E | G251D | S273Y | | | 153 | 10 | 1479 |
| 191 | H76Q | S164G | L222I | N249D | G251D | S273Y | V309I | | | 112 | 19 | 606 |
| 192 | K19T | D59N | H76Q | S164G | L222I | N249D | S273Y | | | 152 | 42 | 363 |
| 193 | Y21S | D59N | H76Q | S164G | L222I | S226T | G251D | S273Y | V309I | 107 | 32 | 340 |
| 194 | H76Q | S164G | L166V | L222I | R242E | G251D | S273Y | | | 132 | 14 | 949 |
| 195 | D59N | H76Q | I96L | S164G | L222I | S226T | N249D | G251D | S273Y | 96 | 19 | 498 |
| 196 | D59N | H76Q | L130I | S164G | L166V | G251D | S273Y | V309I | | 76 | 24 | 316 |
| 197 | D59N | S132A | S164G | L222I | R242E | N249D | G251D | S273Y | | 138 | 38 | 365 |
| 198 | H76Q | I96L | G251D | S273Y | V309I | | | | | 71 | 16 | 443 |
| 199 | D59N | H76Q | L130I | S164G | G251D | V309I | | | | 54 | 18 | 309 |
| 200 | K19T | D59N | S164G | L166V | L222I | S226T | G251D | S273Y | | 107 | 31 | 342 |
| 201 | D59N | H76Q | I96L | S132A | S164G | L222I | S226T | G251D | S273Y | 96 | 23 | 426 |
| 202 | K19T | D59N | H76Q | I96L | S164G | L166V | L222I | G251D | S273Y | 90 | 41 | 218 |
| 203 | K19T | D59N | H76Q | L130I | S164G | L222I | S226T | G251D | S273Y | 64 | 21 | 309 |
| 204 | K19T | D59N | H76Q | S132A | L222I | G251D | S273Y | V309I | | 141 | 48 | 294 |
| 205 | H76Q | L130I | L222I | S226T | G251D | S273Y | | | | 124 | 38 | 322 |
| 206 | K19T | Y21S | D59N | H76Q | L130I | S164G | L222I | S273Y | | 75 | 25 | 295 |
| 207 | Y21S | D59N | H76Q | I96L | S164G | L222I | N249D | G251D | S273Y | 129 | 17 | 762 |
| 208 | K19T | D59N | H76Q | S164G | R242E | N249D | G251D | S273Y | | 129 | 15 | 879 |
| 209 | D59N | H76Q | S164G | L222I | S226T | R242E | | | | 124 | 30 | 417 |
| 210 | D59N | H76Q | I96L | S132A | S164G | L166V | L222I | G251D | S273Y | 136 | 21 | 657 |
| 211 | D59N | H76Q | S132A | S164G | L166V | S273Y | | | | 131 | 31 | 423 |
| 212 | Y21S | D59N | S164G | L222I | S226T | N249D | G251D | S273Y | | 92 | 48 | 190 |
| 213 | D59N | H76Q | L130I | S132A | S164G | L222I | R242E | G251D | S273Y | 108 | 24 | 441 |
| 214 | D59N | H76Q | S164G | L166V | L222I | N249D | G251D | S273Y | V309I | 111 | 65 | 171 |
| 215 | D59N | H76Q | I96L | S164G | L222I | S226T | G251D | S273Y | V309I | 87 | 24 | 369 |
| 216 | K19T | D59N | H76Q | L166V | L222I | R242E | G251D | S273Y | | 146 | 30 | 494 |
| 217 | Y21S | D59N | H76Q | I96L | L222I | S273Y | | | | 118 | 52 | 228 |
| 218 | D59N | H76Q | I96L | L130I | S164G | L222I | N249D | G251D | S273Y | 75 | 23 | 323 |
| 219 | L130I | S164G | L222I | S273Y | | | | | | 46 | 38 | 121 |
| 220 | K19T | Y21S | H76Q | S164G | L222I | G251D | S273Y | | | 65 | 28 | 228 |
| 221 | Y21S | D59N | H76Q | L130I | S132A | S164G | L222I | G251D | S273Y | 65 | 31 | 213 |
| 222 | D59N | H76Q | S226T | R242E | G251D | S273Y | | | | 102 | 37 | 273 |

In table 1 are shown camel chymosin variants with data on specific clotting activity (C), unspecific proteolytic activity (P) as well as the C/P ratio. Out of 43 variants 17 reveal between 10% and 50% increased specific clotting activity compared to wild type camel chymosin (CHY-MAX M). All variants have significantly increased C/P ratios, with the best one, 190, showing a ca. 15x improvement compared to wild type camel chymosin.

Mutational Analysis of Multi-Substitution Library 1

A statistical analysis of the positional and mutational effects on specific clotting activity (C) and the C/P ratio was performed based on the proteolytic data of library 1. The most beneficial mutations for increased specific clotting and C/P are shown in tables 2 and 3, respectively.

TABLE 2

Mutational contributions (mean) to increased specific clotting activity and standard deviations (sd) based on statistical analysis.

| mutation | mean | sd |
|---|---|---|
| R242E | 1.98E−01 | 2.47E−02 |
| L222I | 1.09E−01 | 3.35E−02 |
| D59N | 6.06E−02 | 3.12E−02 |
| S273Y | 6.06E−02 | 3.47E−02 |
| K19T | 5.13E−02 | 2.65E−02 |
| V309I | 4.37E−02 | 2.92E−02 |
| S132A | 4.18E−02 | 2.46E−02 |
| N249D | 3.85E−02 | 2.54E−02 |
| I96L | 3.38E−02 | 2.59E−02 |

Based on the results shown in table 2 it is concluded that mutations K19T, D59N, I96L, S132A, L222I, R242E, N249D, S273Y, and V309I increase the specific clotting activity of chymosin. It can consequently be expected that these mutations enable a lower dosing of chymosin in cheese manufacturing.

TABLE 3

Mutational contributions (mean) to increased C/P ratio and standard deviations (sd) based on statistical analysis.

| mutation | mean | sd |
|---|---|---|
| R242E | 2.12E−01 | 2.82E−02 |
| I96L | 1.20E−01 | 2.81E−02 |
| H76Q | 9.10E−02 | 2.16E−02 |
| S164G | 8.59E−02 | 2.19E−02 |
| S273Y | 7.77E−02 | 2.01E−02 |
| G251D | 3.59E−02 | 1.99E−02 |

Based on the results shown in table 3 it is concluded that mutations H76Q, I96L, S164G, R242E, G251D, and S273Y increase the C/P ratio of chymosin. It can consequently be expected that these mutations result in increased yields during cheese manufacturing using the respective chymosin variants.

Multi-Substitution Library 2

Another set of camel chymosin variants, each having multiple substitutions compared to wild type, were generated and analyzed as described above. All variants have an amino acid sequence identical to camel chymosin (SEQ ID NO:2), except for the variations mentioned in the table. Camel chymosin (CHY-MAX M) is included as reference.

Clotting activities were determined using the REMCAT method.

TABLE 4

Enzymatic activities of camel chymosin variants 223-269. Numbers are given in % cleavage of wild type camel chymosin (CHY-MAX M).

| variant CHY-MAX M | mutations | | | | | | | | | Clotting (C) 100 | Proteolytic (P) 100 | C/P 100 |
|---|---|---|---|---|---|---|---|---|---|---|---|---|
| 223 | K19T | D59N | I96L | S164G | L222I | G251D | | | | 89 | 37 | 242 |
| 224 | Y11I | K19T | D59N | I96V | L222I | R242D | G251D | | | 82 | 31 | 262 |
| 225 | K19S | D59N | I96V | S164G | G251D | | | | | 72 | 40 | 182 |
| 226 | K19S | I96L | S164G | L166V | L222I | R242E | | | | 91 | 38 | 242 |
| 227 | K19T | D59N | I96L | S164G | L166V | L222I | R242D | G251D | L253I | 92 | 24 | 378 |
| 228 | D59N | I96L | S164G | L222I | R242E | L253I | I263L | | | 108 | 23 | 467 |
| 229 | K19T | D59N | E83T | I96L | L222I | G251D | I263L | | | 99 | 106 | 93 |
| 230 | Y11I | K19T | D59N | S164G | L222I | G251D | I263V | | | 54 | 16 | 343 |
| 231 | K19T | D59N | I96L | S164G | L166I | G251D | L253V | | | 63 | 30 | 206 |
| 232 | K19T | I96V | S164G | L222I | N249D | G251D | L253I | | | 56 | 29 | 193 |
| 233 | K19T | I96L | L222I | R242E | L253I | | | | | 125 | 57 | 220 |
| 234 | K19T | E83S | I96L | S164G | L222I | R242E | G251D | L253I | | 83 | 35 | 235 |
| 235 | D59N | E83T | I96L | S164N | L222V | G251D | | | | 42 | 53 | 80 |
| 236 | K19S | D59N | I96L | S164G | L222I | R242E | N249E | G251D | | 130 | 28 | 459 |
| 237 | K19T | I96L | S164G | L166V | L222I | N249D | I263L | | | 65 | 30 | 217 |
| 238 | D59N | I96L | L166V | L222I | R242E | G251D | | | | 178 | 51 | 347 |
| 239 | K19T | D59N | E83T | S164G | L166V | L222I | R242D | G251D | | 101 | 43 | 235 |
| 240 | Y11I | K19T | D59N | E83S | I96L | S164G | L222I | N249D | | 53 | 60 | 87 |
| 241 | K19T | E83T | I96L | S164G | L222I | R242E | L253V | | | 97 | 37 | 261 |
| 242 | K19T | D59N | I96L | S164G | L166I | L222I | R242E | N249D | | 129 | 21 | 623 |
| 243 | Y11V | K19T | D59N | I96L | S164G | L166V | L222I | R242E | G251D | L253I | 130 | 17 | 759 |
| 244 | K19T | I96L | S164N | L222I | R242E | I263L | | | | 51 | 22 | 236 |
| 245 | Y11V | D59N | I96L | S164G | L222I | G251D | L253V | | | 63 | 24 | 265 |
| 246 | K19T | D59N | I96V | S164G | L166V | L222I | R242E | I263L | | 98 | 28 | 347 |
| 247 | Y11V | K19T | D59N | I96L | S164N | L166I | L222I | G251D | | 32 | 16 | 202 |
| 248 | K19T | I96L | S164G | L166V | L222I | R242E | N249D | G251D | I263V | 105 | 19 | 566 |
| 249 | K19T | I96L | S164G | R242E | L253I | | | | | 73 | 14 | 516 |
| 250 | K19S | D59N | E83S | I96L | S164N | L222I | G251D | | | 47 | 64 | 74 |
| 251 | K19T | D59N | I96L | S164G | L222V | N249E | G251D | I263V | | 79 | 27 | 293 |
| 252 | K19T | D59N | I96L | S164G | L222I | N249E | G251D | L253V | I263L | 69 | 21 | 332 |
| 253 | Y11I | K19T | I96L | S164G | L222V | R242E | G251D | | | 58 | 2 | 3265 |
| 254 | I96L | S164G | L222I | R242E | N249D | G251D | I263L | | | 82 | 14 | 601 |
| 255 | K19T | D59N | I96L | S164G | L166I | L222I | R242D | G251D | I263V | 108 | 25 | 427 |
| 256 | K19T | D59N | I96L | S164G | L222V | R242E | N249D | L253I | | 111 | 19 | 574 |
| 257 | H76Q | I96L | S164G | L222I | R242E | G251D | S273Y | | | 128 | 8 | 1597 |
| 258 | K19T | E83S | I96L | L222I | R242E | N249D | G251D | L253I | | 95 | 30 | 315 |
| 259 | I96L | S164G | L166V | L222I | R242E | N249D | I263L | | | 104 | 26 | 405 |
| 260 | Y11V | K19T | E83S | I96L | S164G | L166V | L222I | R242E | G251D | | 97 | 14 | 676 |
| 261 | Y11V | K19T | I96L | S164G | L166V | L222I | R242E | | | 94 | 19 | 491 |
| 262 | Y11V | E83S | I96L | S164G | L222I | R242E | G251D | L253I | I263L | 61 | 18 | 332 |
| 263 | Y11V | I96L | S164G | L222I | R242E | N249D | L253I | I263L | | 67 | 7 | 961 |
| 264 | K19T | I96L | S164G | L166V | L222I | R242E | N249D | I263L | | 75 | 50 | 149 |
| 265 | Y11V | E83S | I96L | S164G | L222I | R242E | L253I | I263L | | 62 | 28 | 222 |
| 266 | K19T | E83S | I96L | S164G | L166V | L222I | R242E | N249D | G251D | L253I | 97 | 32 | 302 |
| 267 | I96L | S164G | L222I | R242E | G251D | S274Y | | | | 110 | 19 | 569 |
| 268 | H76Q | I96L | S164G | L222I | R242E | G251D | | | | 102 | 10 | 1054 |
| 269 | I96L | S164G | L222I | R242E | G251D | | | | | 101 | 22 | 465 |

In table 4 are shown camel chymosin variants with data on specific clotting activity (C), unspecific proteolytic activity (P) as well as the C/P ratio. Out of 47 variants, 8 reveal between 10% and 78% increased specific clotting activity compared to wild type camel chymosin (CHY-MAX M). While 43 variants have significantly increased C/P ratios, the best one, 253, shows a ca. 33x improvement compared to wild type camel chymosin.

Mutational Analysis of Multi-Substitution Library 2

A statistical analysis of the positional and mutational effects on specific clotting activity (C) and the C/P ratio was performed based on the proteolytic data of library 2. The most beneficial mutations for increased specific clotting and C/P are shown in tables 5 and 6, respectively.

TABLE 5

Mutational contributions (mean) to increased specific clotting activity and standard deviations (sd) based on statistical analysis.

| mutation | mean | sd |
| --- | --- | --- |
| R242E | 4.00E−01 | 3.19E−02 |
| D59N | 2.94E−01 | 2.26E−02 |
| N249E | 1.47E−01 | 3.22E−02 |
| L166V | 1.27E−01 | 2.70E−02 |
| S273Y | 1.23E−01 | 2.94E−02 |
| L222I | 1.07E−01 | 3.53E−02 |
| H76Q | 5.93E−02 | 2.94E−02 |
| N249D | 4.26E−02 | 2.38E−02 |

Based on the results shown in table 5 it is concluded that mutations D59N, H76Q, L166V, L222I, R242E, N249D, N249E, and S273Y increase the specific clotting activity of chymosin. It can consequently be expected that these mutations enable a lower dosing of chymosin in cheese manufacturing.

TABLE 6

Mutational contributions (mean) to increased C/P ratio and standard deviations (sd) based on statistical analysis.

| mutation | mean | sd |
| --- | --- | --- |
| R242E | 4.13E−01 | 2.20E−02 |
| H76Q | 2.50E−01 | 3.24E−02 |
| Y11I | 2.49E−01 | 6.43E−02 |
| S164G | 2.27E−01 | 2.07E−02 |
| G251D | 2.10E−01 | 2.65E−02 |
| R242D | 1.85E−01 | 2.69E−02 |
| L222V | 1.75E−01 | 4.53E−02 |
| Y11V | 1.75E−01 | 2.83E−02 |
| S273Y | 8.29E−02 | 3.35E−02 |
| L166I | 7.64E−02 | 2.91E−02 |
| I96L | 3.85E−02 | 2.59E−02 |
| K19T | 3.85E−02 | 2.43E−02 |

Based on the results shown in table 6 it is concluded that mutations Y11I, Y11V, K19T, H76Q, I96L, S164G, L166I, L222V, R242D, R242E, G251D, and S273Y increase the C/P ratio of chymosin. It can consequently be expected that these mutations result in increased yields during cheese manufacturing using the respective chymosin variants.

Structure-Based Variations in Camel Chymosin

Variants of camel chymosin (SEQ ID NO:2) were made with amino acid changes in positions determined by protein structural analysis (Tab. 7). Mutations N100Q and N291Q were introduced into both N-glycosylation sites of these variants and the reference camel chymosin (CamUGly) to yield non-glycosylated, homogeneous protein samples.

Clotting activities were determined using the μIMCU method.

TABLE 7

Enzymatic activities of camel chymosin variants 271-308. Numbers are given in % cleavage of non-glycosylated camel chymosin (CamUGly).
Table 7 CamBov

| variant CamUGly | mutations | | Clotting (C) 100 | Proteolytic (P) 100 | C/P 100 |
| --- | --- | --- | --- | --- | --- |
| 271 | V221K | N100Q N291Q | 47 | 61 | 77 |
| 272 | D290E | N100Q N291Q | 92 | 100 | 92 |
| 273 | V136I | N100Q N291Q | 80 | 90 | 89 |
| 274 | E240Q | N100Q N291Q | 84 | 144 | 58 |
| 276 | G289S | N100Q N291Q | 93 | 107 | 86 |
| 277 | N292H | N100Q N291Q | 95 | 93 | 100 |
| 278 | L295K | N100Q N291Q | 102 | 70 | 146 |
| 279 | V136E | N100Q N291Q | 102 | 102 | 100 |
| 280 | D290L | N100Q N291Q | 44 | 198 | 22 |
| 281 | F119Y | N100Q N291Q | 8 | 45 | 18 |
| 282 | Q280E | N100Q N291Q | 79 | 72 | 110 |
| 283 | F282E | N100Q N291Q | 93 | 80 | 116 |
| 284 | N249D | N100Q N291Q | 118 | 84 | 140 |
| 285 | R254S | N100Q N291Q | 47 | 94 | 50 |
| 286 | R242E | N100Q N291Q | 114 | 67 | 170 |
| 288 | V203R | N100Q N291Q | 99 | 113 | 88 |
| 289 | N249R | N100Q N291Q | 76 | 108 | 70 |
| 290 | H56K | N100Q N291Q | 99 | 133 | 74 |
| 291 | S74D | N100Q N291Q | 94 | 87 | 108 |
| 292 | A131D | N100Q N291Q | 17 | 39 | 44 |
| 293 | Y190A | N100Q N291Q | 3 | 33 | 9 |
| 294 | I297A | N100Q N291Q | 26 | 37 | 70 |
| 302 | Y21S | N100Q N291Q | 97 | 87 | 111 |
| 303 | L130I | N100Q N291Q | 77 | 82 | 95 |
| 306 | G251D | N100Q N291Q | 100 | 81 | 123 |
| 307 | Y243E | N100Q N291Q | 86 | 58 | 149 |
| 308 | S273D | N100Q N291Q | 102 | 98 | 104 |

Based on the results shown in table 7 it is concluded that mutations Y21S, S74D, R242E, Y243E, N249D, G251D, S273D, Q280E, F282E, and L295K increase the C/P ratio of chymosin. Mutations R242E and N249D also result in increased specific clotting activity. Seven out of ten variants with increased C/P ratios shown in table 7 bear mutations (R242E, N249D, G251D, Y243E, S273D, Q280E, F282E) in a distinct region on the protein surface that is located in proximity to the binding cleft as seen in FIG. 2. This region has been suggested to support binding of the κ-casein substrate by interacting with its positively charged sequence Arg96 to His102 (references 5, 16-18) in positions P10 to P4 (reference 10). The negative charges introduced with the mutations may strengthen these interactions, resulting in increased specificity for κ-casein (C/P). The results show that single amino acid substitutions in this region can increase C/P significantly.

Negative Charge Combinations in Camel Chymosin

More variants of camel chymosin (SEQ ID NO:2) were made with combinations of mutations that introduce negative charges into the surface region described above (R242E, Y243E, G251D, N252D, R254E, S273D, Q280E). Mutations N100Q and N291Q were introduced into both N-glycosylation sites of these variants and the reference camel chymosin (CamUGly) to yield non-glycosylated, homogeneous protein samples (Tab. 8).

Clotting activities were determined using the μIMCU method.

TABLE 8

Enzymatic activities of camel chymosin variants 309-323. Numbers are given in % cleavage of non-glycosylated camel chymosin (CamUGly).

| variant | mutations | | | | | Clotting (C) | Proteolytic (P) | C/P |
|---|---|---|---|---|---|---|---|---|
| CamUGly | | | | N100Q | N291Q | 100 | 100 | 100 |
| 309 | R242E | Q280E | | N100Q | N291Q | 133 | 59 | 225 |
| 310 | R242E | N252D | | N100Q | N291Q | 136 | 63 | 216 |
| 311 | N252D | Q280E | | N100Q | N291Q | 108 | 96 | 112 |
| 312 | Y243E | Q280E | | N100Q | N291Q | 112 | 71 | 158 |
| 313 | Y243E | N252D | | N100Q | N291Q | 91 | 77 | 117 |
| 314 | R254E | Q280E | | N100Q | N291Q | 106 | 84 | 127 |
| 315 | S273D | Q280E | | N100Q | N291Q | 77 | 51 | 150 |
| 316 | R242E | G251D | | N100Q | N291Q | 107 | 72 | 148 |
| 317 | R242E | G251D | Q280E | N100Q | N291Q | 138 | 84 | 164 |
| 318 | R242E | S273D | Q280E | N100Q | N291Q | 136 | 98 | 139 |
| 319 | N252D | S273D | Q280E | N100Q | N291Q | 115 | 67 | 171 |
| 320 | G251D | S273D | Q280E | N100Q | N291Q | 114 | 64 | 176 |
| 321 | R242E | R254E | Q280E | N100Q | N291Q | 134 | 66 | 202 |
| 322 | R242E | R254E | S273D | Q280E | N100Q N291Q | 126 | 60 | 211 |
| 323 | Y243E | R254E | S273D | N100Q | N291Q | 103 | 71 | 144 |

All variants shown in table 8 reveal increased C/P ratios compared to non-glycosylated camel chymosin. Several of these variants (309, 310, 321, 322, 323) had even higher C/P than the best variant with single negative charge mutation (286). It is concluded that the C/P-increasing effect, caused by introducing negative charges into the P10-P4 interacting region on the chymosin structure, can be further enhanced by combinations of the respective mutations.

Structure-Based Variations in Bovine Chymosin

Variants of bovine chymosin (SEQ ID NO:1) were made with amino acid changes in positions determined by protein structural analysis (Table 9). Mutations N252Q and N291Q were introduced into both N-glycosylation sites of these variants and the reference bovine chymosin (BovUGly) to yield non-glycosylated, homogeneous protein samples.

Clotting activities were determined using the µIMCU method.

TABLE 9

Enzymatic activities of bovine chymosin variants 325-346. Numbers are given in % cleavage of non-glycosylated bovine chymosin (BovUGly).

| variant | mutations | | Clotting (C) | Proteolytic (P) | C/P |
|---|---|---|---|---|---|
| BovUGly | N252Q | N291Q | 100 | 100 | 100 |
| 325 | V223F | N252Q N291Q | 54 | 130 | 41 |
| 327 | A117S | N252Q N291Q | 75 | 76 | 96 |
| 329 | Q242R | N252Q N291Q | 76 | 166 | 45 |
| 330 | Q278K | N252Q N291Q | 94 | 112 | 83 |
| 332 | H292N | N252Q N291Q | 96 | 71 | 133 |
| 333 | Q294E | N252Q N291Q | 99 | 79 | 123 |
| 334 | K295L | N252Q N291Q | 106 | 182 | 58 |
| 335 | D249N | N252Q N291Q | 89 | 129 | 68 |
| 337 | G244D | N252Q N291Q | 100 | 106 | 93 |
| 338 | Q56H | N252Q N291Q | 110 | 140 | 77 |
| 339 | L32I | N252Q N291Q | 86 | 124 | 69 |
| 340 | K71E | N252Q N291Q | 44 | 50 | 86 |
| 341 | P72T | N252Q N291Q | 103 | 172 | 59 |
| 342 | Q83T | N252Q N291Q | 92 | 103 | 88 |
| 343 | V113F | N252Q N291Q | 42 | 44 | 95 |
| 344 | E133S | N252Q N291Q | 93 | 199 | 46 |
| 345 | Y134G | N252Q N291Q | 106 | 115 | 91 |
| 346 | K71A | N252Q N291Q | 79 | 131 | 60 |

The data in table 9 demonstrate that variations Q56H, Y134G, and K295L lead to increased specific clotting activity and variations H292N and Q294E result in enhanced C/P ratios. Both H292 and Q294 are located in a loop partially covering the substrate binding cleft (FIG. 3), which explains the observed impact of the respective mutations in these positions on casein substrate specificity (C/P). Notably, while substitutions H292N increased C/P and D249N as well as K295L decreased C/P of bovine chymosin, inverse effects on C/P were observed by the respective reverse mutations N292H, N249D, and L295K in camel chymosin (Tab. 7). This demonstrates that these amino acid changes exert similar effects on chymosin specificity across species.

Variations of the camel chymosin N-terminus

Variants of camel chymosin (SEQ ID NO:2) were made with amino acid changes in positions determined by protein structural analysis of the molecular interactions of the N-terminal sequence Y11-D13 within the substrate binding cleft (Tab. 10). Mutations N100Q and N291Q were introduced into both N-glycosylation sites of these variants and the reference camel chymosin (CamUGly) to yield non-glycosylated, homogeneous protein samples.

Clotting activities were determined using the µIMCU method.

TABLE 10

Enzymatic activities of camel chymosin variants 347-366.
Numbers are given in % cleavage of non-glycosylated
camel chymosin (CamUGly).

| variant | | mutations | | | Clotting (C) | Proteolytic (P) | C/P |
|---|---|---|---|---|---|---|---|
| CamUGly | | | N100Q | N291Q | 100 | 100 | 100 |
| 347 | Y11H | | N100Q | N291Q | 76 | 131 | 58 |
| 348 | Y11K | | N100Q | N291Q | 63 | 82 | 76 |
| 349 | Y11R | | N100Q | N291Q | 55 | 277 | 20 |
| 350 | Y11H | D290E | N100Q | N291Q | 74 | 105 | 71 |
| 351 | Y11R | D290E | N100Q | N291Q | 62 | 101 | 62 |
| 352 | Y11F | | N100Q | N291Q | 91 | 146 | 62 |
| 353 | Y11I | | N100Q | N291Q | 96 | 83 | 116 |
| 354 | Y11L | | N100Q | N291Q | 79 | 108 | 74 |
| 355 | Y11V | | N100Q | N291Q | 101 | 64 | 157 |
| 356 | L12F | | N100Q | N291Q | 96 | 147 | 66 |
| 357 | L12I | | N100Q | N291Q | 83 | 91 | 91 |
| 359 | D13N | | N100Q | N291Q | 88 | 131 | 67 |
| 360 | D13Q | | N100Q | N291Q | 100 | 169 | 59 |
| 361 | D13S | | N100Q | N291Q | 88 | 164 | 54 |
| 362 | D13T | | N100Q | N291Q | 62 | 89 | 70 |
| 363 | D13F | | N100Q | N291Q | 73 | 155 | 48 |
| 364 | D13L | | N100Q | N291Q | 82 | 196 | 42 |
| 365 | D13V | | N100Q | N291Q | 49 | 86 | 57 |
| 366 | D13Y | | N100Q | N291Q | 74 | 99 | 75 |

Analysis of the camel chymosin structure guided variations in the N-terminal sequence Y11-D13 as well as in position D290, a potential interaction partner of Y11 (FIG. 4). Since casein substrates compete with the N-terminal chymosin sequence for binding within the binding cleft, amino acid substitutions that change interactions between binding cleft and the motif Y11-D13 are expected to impact enzymatic activity toward various casein substrates and, thus, the C/P ratio. The results of the respective variants 347-366 show strong variation of both specific clotting activity and C/P. Notably, variants 353 and 355 reveal increased C/P ratios. It is therefore concluded that amino acid substitutions Y11I and Y11V result in increased C/P ratios. Since the chymosin binding cleft consists mainly of hydrophobic amino acids (reference 9), both mutations might enhance binding of the N-term in the binding cleft by improved hydrophobic interactions and, thus, inhibit non-specific binding and hydrolysis of caseins (P).

Multi-Substitution Library 3

Another set of camel chymosin variants, each having multiple substitutions compared to wild type, were generated and analyzed as described above. All variants have an amino acid sequence identical to camel chymosin (SEQ ID NO:2), except for the variations mentioned in the table. Camel chymosin (CHY-MAX M) is included as reference.

Clotting activities were determined using the µIMCU method.

TABLE 11

Enzymatic activities of camel chymosin variants 367-416. Numbers
are given in % cleavage of wild type camel chymosin (CHY-MAX M).

| variant CHY-MAX M | | mutations | | | | | Clotting (C) 100 | Proteolytic (P) 100 | C/P 100 |
|---|---|---|---|---|---|---|---|---|---|
| 367 | R67Q | N100Q | L130I | M157L | V248I | N291Q | 46 | 64 | 72 |
| 368 | N100Q | L130I | S132A | M157L | K231N | | 87 | 104 | 83 |
| 369 | R67Q | I96L | L130I | M157L | L222I | M256L | 49 | 56 | 88 |
| 370 | R67Q | L130I | S132A | M157L | R242E | V248I | 23 | 32 | 70 |
| 371 | R67Q | N100Q | M157L | R242E | M256L | | 100 | 62 | 162 |
| 372 | R67Q | G70D | M157L | R242E | V248I | | 89 | 32 | 276 |
| 373 | V32L | R67Q | M157L | L222I | R242E | | 64 | 63 | 102 |
| 374 | Y11V | R67Q | M157L | V248I | M256L | | 71 | 45 | 158 |
| 375 | R67Q | V136I | M157L | L222I | V248I | | 88 | 20 | 449 |
| 376 | L130I | M157L | V248I | M256L | N291Q | | 90 | 80 | 112 |
| 377 | R67Q | I96L | L130I | M157L | K231N | R242E | 124 | 37 | 339 |
| 378 | V32L | R67Q | L130I | M157L | L222I | K231N | 52 | 103 | 51 |
| 379 | L130I | V136I | M157L | L222I | N292H | | 55 | 47 | 118 |
| 380 | R67Q | G70D | M157L | L222I | N291Q | | 117 | 34 | 339 |
| 381 | V32L | R67Q | L130I | K231N | N292H | | 58 | 66 | 87 |
| 382 | Y11V | R67Q | N100Q | L130I | V136I | M157L | 60 | 55 | 109 |
| 383 | R67Q | L130I | L222I | R242E | M256L | | 78 | 27 | 290 |
| 384 | R67Q | M157L | L222I | V248I | N292H | | 83 | 97 | 86 |
| 385 | V32L | R67Q | M157L | M256L | N291Q | | 85 | 143 | 60 |
| 386 | R67Q | L130I | S132A | M157L | L222I | N292H | 78 | 133 | 58 |
| 387 | R67Q | N100Q | L130I | M157L | K231N | N291Q | 59 | 70 | 84 |
| 388 | R67Q | L130I | K231N | V248I | N291Q | | 91 | 87 | 105 |

TABLE 11-continued

Enzymatic activities of camel chymosin variants 367-416. Numbers are given in % cleavage of wild type camel chymosin (CHY-MAX M).

| variant CHY-MAX M | mutations | | | | | Clotting (C) 100 | Proteolytic (P) 100 | C/P 100 |
|---|---|---|---|---|---|---|---|---|
| 389 | Y11V | R67Q | L130I | M157L | L222I | K231N | 63 | 47 | 134 |
| 390 | I45V | L130I | M157L | K231N | R242E | | 108 | 43 | 253 |
| 391 | V32L | R67Q | V136I | M157L | N291Q | | 104 | 84 | 124 |
| 392 | R67Q | N100Q | L130I | D158S | V248I | | 70 | 67 | 105 |
| 393 | I45V | R67Q | L130I | M157L | L222I | K231N | 79 | 54 | 147 |
| 394 | V32L | R67Q | L130I | S132A | M157L | V248I | 74 | 130 | 57 |
| 395 | Y11V | R67Q | L130I | M157L | N291Q | N292H | 74 | 83 | 90 |
| 396 | R67Q | N100Q | L130I | M157L | L222I | K231N | 60 | 81 | 74 |
| 397 | I45V | R67Q | G70D | L130I | S132A | | 68 | 75 | 90 |
| 398 | I45V | R67Q | L130I | V248I | N292H | | 53 | 81 | 66 |
| 399 | Y11V | R67Q | L130I | M157L | L222I | R242E | 106 | 28 | 373 |
| 400 | R67Q | N100Q | D158S | L130I | M157L | L222I | 57 | 58 | 98 |
| 401 | R67Q | L130I | V136I | M157L | K231N | V248I | 71 | 79 | 89 |
| 402 | I45V | R67Q | L130I | L222I | N291Q | | 91 | 89 | 103 |
| 403 | R67Q | G70D | L130I | M157L | K231N | M256L | 89 | 53 | 167 |
| 404 | V32L | R67Q | L130I | M157L | D158S | V248I | 58 | 82 | 71 |
| 405 | R67Q | L130I | M157L | D158S | R242E | N291Q | 92 | 16 | 556 |
| 406 | R67Q | L130I | M157L | D158S | K231N | N292H | 53 | 74 | 72 |
| 407 | R67Q | L130I | V248I | M256L | N292H | | 58 | 107 | 55 |
| 408 | V32L | R67Q | I96L | L130I | M157L | V248I | 35 | 76 | 46 |
| 409 | R67Q | I96L | N100Q | L130I | M157L | N292H | 96 | 36 | 263 |
| 410 | V32L | R67Q | G70D | N100Q | M157L | | 68 | 66 | 104 |
| 411 | V32L | R67Q | L130I | M157L | K231N | M256L | 102 | 18 | 574 |
| 412 | R67Q | I96L | M157L | L222I | K231N | | 120 | 55 | 220 |
| 413 | R67Q | M157L | L222I | K231N | V248I | | 124 | 46 | 268 |
| 414 | R67Q | L130I | M157L | R242E | M256L | N292H | 115 | 59 | 196 |
| 415 | R67Q | L222I | K231N | V248I | | | 82 | 67 | 123 |
| 416 | R67Q | S132A | L222I | K231N | R242E | V248I | 129 | 42 | 306 |

In table 11 are shown camel chymosin variants with data on specific clotting activity (C), unspecific proteolytic activity (P) as well as the C/P ratio. Out of 50 variants 6 reveal between 10% and 29% increased specific clotting activity compared to wild type camel chymosin (CHY-MAX M). While 23 variants have more than 10% increased C/P ratios, the best one, 411, shows a ca. 6x improvement compared to wild type camel chymosin (CHY-MAX M).

Mutational Analysis of Multi-Substitution Library 3

A statistical analysis of the positional and mutational effects on clotting activity (C) and the C/P ratio was performed based on the proteolytic data of library 3. The most beneficial mutations for increased clotting and C/P are shown in tables 12 and 13, respectively.

TABLE 12

Mutational contributions (mean) to increased clotting activity and standard deviations (sd) based on statistical analysis.

| mutation | mean | sd |
|---|---|---|
| R242E | 4.63E-01 | 4.21E-02 |
| I96L | 2.31E-01 | 4.82E-02 |
| N291Q | 1.67E-01 | 3.97E-02 |
| K231N | 1.34E-01 | 3.52E-02 |
| M256L | 1.28E-01 | 4.44E-02 |
| S132A | 1.04E-01 | 3.35E-02 |
| M157L | 7.99E-02 | 3.49E-02 |

Based on the results shown in table 12 it is concluded that mutations I96L, S132A, M157L, K231N, R242E, M256L, and N291Q increase the specific clotting activity of chymosin. It can consequently be expected that these mutations enable a lower dosing of chymosin in cheese manufacturing.

TABLE 13

Mutational contributions (mean) to increased C/P ratio and standard deviations (sd) based on statistical analysis.

| mutation | mean | sd |
|---|---|---|
| R242E | 6.66E-01 | 4.23E-02 |
| G70D | 3.32E-01 | 5.72E-02 |
| Y11V | 2.06E-01 | 3.61E-02 |
| K231N | 1.45E-01 | 2.92E-02 |
| L222I | 1.09E-01 | 3.71E-02 |
| V136I | 1.02E-01 | 4.53E-02 |
| I96L | 9.84E-02 | 6.02E-02 |
| N291Q | 4.78E-02 | 4.20E-02 |

Based on the results shown in table 13 it is concluded that mutations Y11V, G70D, I96L, V136I, L222I, K231N, R242E, and N291Q increase the C/P ratio of chymosin. It can consequently be expected that these mutations result in increased yields during cheese manufacturing using the respective chymosin variants.

Multi-Substitution Library 4

Another set of camel chymosin variants, each having multiple substitutions compared to wild type, were generated and analyzed as described above. All variants have an amino acid sequence identical to camel chymosin (SEQ ID NO:2), except for the variations mentioned in the table. Camel chymosin (CHY-MAX M) is included as reference.

Clotting activities were determined using the REMCAT method.

TABLE 14

Enzymatic activities of camel chymosin variants 417-461. Numbers are given in % cleavage of wild type camel chymosin (CHY-MAX M).

| variant CHY-MAX M | mutations | | | | | | | | | Clotting (C) 100 | Proteolytic (P) 100 | C/P 100 |
|---|---|---|---|---|---|---|---|---|---|---|---|---|
| 417 | Y11V | K19T | D59N |      | S164G | L166V | L222I | R242E | N249E | G251D |       | 132 | 20 | 651 |
| 418 | Y11V | K19T | D59N | I96L | S164G | L166I | L222I | R242E | N249E | G251D |       | 114 | 21 | 556 |
| 419 | Y11I | K19T | D59N | I96L | S164G | L166V | L222I | R242E | N249E | G251D |       | 108 | 20 | 554 |
| 420 | Y11I | K19T | D59N | I96L | S164G | L166I | L222I | R242E |       | G251D |       | 98 | 11 | 898 |
| 421 | Y11V | K19T | D59N | I96L |       | L166V | L222V | R242E | N249E | G251D | L253I | 132 | 84 | 156 |
| 422 | Y11V | K19T | D59N | I96L | S164G | L166V |       | R242E |       |       |       | 105 | 13 | 802 |
| 423 | Y11V | K19T | D59N | I96L | S164G |       | L222V | R242E |       | G251D |       | 89 | 8 | 1131 |
| 424 | Y11V | K19T | D59N | I96L | S164G | L166I |       | R242E | N249E | G251D | L253I | 93 | 8 | 1111 |
| 425 | Y11V | K19T | D59N | I96L | S164G | L166V | L222V | R242E | N249E | G251D |       | 105 | 18 | 572 |
| 426 | Y11V | K19T | D59N | I96L | S164G | L166I | L222V | R242E | N249E | G251D | L253I | 93 | 18 | 512 |
| 427 | Y11V | K19T | D59N |      |       | L166V | L222I | R242E | N249E | G251D | L253I | 137 | 42 | 323 |
| 428 | Y11V | K19T | D59N | I96L | S164G | L166V | L222I | R242E | N249E |       |       | 120 | 15 | 803 |
| 429 | Y11V | K19T | D59N |      | S164G | L166I | L222I | R242E |       | G251D |       | 107 | 17 | 630 |
| 430 | Y11V | K19T | D59N | I96L | S164G |       |       | R242E |       | G251D |       | 89 | 11 | 801 |
| 431 | Y11V |      | D59N | I96L | S164G | L166I | L222V | R242E |       | G251D | L253I | 79 | 28 | 283 |
| 432 | Y11V |      | D59N | I96L | S164G | L166I | L222I | R242E |       | G251D |       | 102 | 24 | 432 |
| 433 | Y11I |      | D59N | I96L | S164G | L166V | L222V | R242E |       | G251D | L253I | 97 | 25 | 392 |
| 434 | Y11V | K19T | D59N | I96L | S164G |       | L222I | R242E | N249E | G251D |       | 99 | 33 | 301 |
| 435 | Y11V | K19T | D59N | I96L | S164G | L166I | L222V | R242E |       | G251D |       | 88 | 17 | 514 |
| 436 | Y11V | K19T | D59N | I96L | S164G | L166V | L222V | R242E | N249E |       | L253I | 95 | 10 | 949 |
| 437 | Y11V | K19T | D59N | I96L | S164G | L166I | L222V | R242E | N249E | G251D |       | 114 | 22 | 520 |
| 438 | Y11I | K19T |      | I96L | S164G | L166V |       | R242E | N249E | G251D |       | 93 | 7 | 1262 |
| 439 | Y11V | K19T | D59N | I96L | S164G | L166V | L222V | R242E |       | G251D |       | 108 | 26 | 423 |
| 440 | Y11V | K19T | D59N | I96L | S164G |       | L222V | R242E | N249E | G251D |       | 105 | 9 | 1196 |
| 441 | Y11I | K19T |      |      |       |       | L222V | R242E | N249E | G251D |       | 122 | 26 | 469 |
| 442 | Y11V | K19T |      | I96L |       |       | L222V | R242E | N249E | G251D |       | 105 | 21 | 503 |
| 443 | Y11I | K19T | D59N | I96L | S164G | L166V | L222V | R242E | N249E | G251D |       | 105 | 18 | 595 |
| 444 | Y11V | K19T |      | I96L | S164G | L166V | L222V | R242E | N249E | G251D |       | 96 | 8 | 1242 |
| 445 | Y11I | K19T | D59N | I96L | S164G | L166I | L222V | R242E | N249E | G251D |       | 82 | 12 | 707 |
| 446 | Y11I |      | I96L |      | S164G | L166V | L222V | R242E | N249E | G251D |       | 95 | 16 | 579 |
| 447 | Y11I | K19T | D59N | I96L | S164G |       | L222V | R242E | N249E |       |       | 90 | 11 | 790 |
| 448 | Y11I | K19T | D59N | I96L |       | S164G | L222V | R242E | N249E | G251D |       | 153 | 40 | 381 |
| 449 | Y11I | K19T | D59N | I96L | S164G |       | L222I | R242E |       |       |       | 89 | 16 | 564 |
| 450 | Y11I | K19T | D59N | I96L | S164G | L166V |       | R242E |       | G251D |       | 88 | 5 | 1686 |
| 451 | Y11I | K19T | D59N |      | S164G | L166I | L222V | R242E |       | G251D |       | 93 | 21 | 440 |
| 452 | Y11I |      | I96L |      |       |       | L222V | R242E | N249E | G251D |       | 122 | 22 | 566 |
| 453 | Y11I |      | I96L |      | S164G |       | L222I | R242E |       |       |       | 74 | 5 | 1375 |
| 454 | Y11V | K19T |      | I96L |       | L166V | L222V | R242E |       | G251D |       | 119 | 52 | 228 |
| 455 | Y11I |      | D59N | I96L | S164G |       | L222I | R242E |       | G251D |       | 105 | 9 | 1139 |
| 456 | Y11I |      | D59N | I96L | S164G |       | L222V | R242E | N249E | G251D |       | 95 | 15 | 615 |
| 457 | Y11I | K19T | D59N | I96L | S164G | L166I |       | R242E | N249E | G251D |       | 101 | 7 | 1419 |
| 458 | Y11I |      | D59N | I96L | S164G | L166V | L222V | R242E |       | G251D |       | 89 | 16 | 572 |
| 459 | Y11V | K19T | D59N | I96L |       | L222V | R242E |       | G251D |       |       | 143 | 62 | 230 |
| 460 | Y11I | K19T |      |      | S164G | L166I | L222V | R242E | N249E | G251D |       | 80 | 13 | 625 |
| 461 | Y11I |      | D59N | I96L | S164G | L166V | L222V | R242E | N249E | G251D |       | 96 | 35 | 273 |

In table 14 are shown camel chymosin variants with data on specific clotting activity (C), unspecific proteolytic activity (P) as well as the C/P ratio. Out of 45 variants 11 reveal between 14% and 53% increased specific clotting activity compared to wild type camel chymosin (CHY-MAX M). While all 45 variants have more than 10% increased C/P ratios, the best one, 450, shows a ca. 17× improvement compared to wild type camel chymosin (CHY-MAX M).

Mutational Analysis of Multi-Substitution Library 4

A statistical analysis of the positional and mutational effects on clotting activity (C) and the C/P ratio was performed based on the proteolytic data of library 4. The most beneficial mutations for increased clotting and C/P are shown in tables 15 and 16, respectively.

TABLE 15

Mutational contributions (mean) to increased clotting activity and standard deviations (sd) based on statistical analysis.

| mutation | mean | sd |
|---|---|---|
| D59N | 3.99E−01 | 3.48E−02 |
| L222I | 2.05E−01 | 2.64E−02 |
| L166V | 1.92E−01 | 2.39E−02 |
| N249E | 1.45E−01 | 1.88E−02 |
| G251D | 9.79E−02 | 2.29E−02 |
| Y11V | 8.54E−02 | 1.56E−02 |
| R242E | 5.14E−02 | 2.06E−02 |

Based on the results shown in table 15 it is concluded that mutations Y11V, D59N, L166V, L222I, R242E, N249E, and G251D increase the specific clotting activity of chymosin. It can consequently be expected that these mutations enable a lower dosing of chymosin in cheese manufacturing.

TABLE 16

Mutational contributions (mean) to increased C/P ratio and standard deviations (sd) based on statistical analysis.

| mutation | mean | sd |
|---|---|---|
| S164G | 7.51E−01 | 4.50E−02 |
| K19T | 2.85E−01 | 4.93E−02 |
| I96L | 2.43E−01 | 4.16E−02 |
| R242E | 2.25E−01 | 7.12E−02 |
| L253I | 2.22E−01 | 4.61E−02 |
| Y11I | 1.30E−01 | 4.93E−02 |
| N249E | 9.52E−02 | 3.86E−02 |
| Y11V | 9.49E−02 | 3.55E−02 |

Based on the results shown in table 16 it is concluded that mutations Y11I, Y11V, K19T, I96L, S164G, R242E, N249E, and L253I increase the C/P ratio of chymosin. It can consequently be expected that these mutations result in in-creased yields during cheese manufacturing using the respective chymosin variants.

Selected variants from multi-substitution library 4 were fermented again in 70L followed by purification and characterization regarding their proteolytic profile (table 17).

TABLE 17

Enzymatic activities of selected camel chymosin variants from 70L fermentation. Numbers are given in % cleavage of wild type camel chymosin (CHY-MAX M).

| variant CHY-MAX M | mutations | | | | | | | | | | Clotting (C) 100 | Proteolytic (P) 100 | C/P 100 |
|---|---|---|---|---|---|---|---|---|---|---|---|---|---|
| 433 | Y11I | D59N | I96L | S164G | L166V | L222V | R242E | G251D | L253I | | 151 | 11 | 1356 |
| 436 | Y11V | K19T | D59N | I96L | S164G | L166V | L222V | R242E | N249E | L253I | 188 | 9 | 2007 |
| 453 | Y11I | I96L | S164G | L222I | R242E | | | | | | 153 | 8 | 1893 |
| 457 | Y11I | K19T | D59N | I96L | S164G | L222I | R242E | N249E | G251D | | 217 | 7 | 3002 |

In table 17 are shown camel chymosin variants from 70L fermentation with data on specific clotting activity (C), unspecific proteolytic activity (P) as well as the C/P ratio. All 4 variants reveal between 51% and 117% increased specific clotting activity compared to wild type camel chymosin (CHY-MAX M). While all 4 variants have more than 13-fold increased C/P ratios, the best one, 457, shows a ca. 30x improvement compared to wild type camel chymosin (CHY-MAX M).

REFERENCES

1. A. Kumar, S. Grover, J. Sharma, V. K. Batish, *Crit. Rev. Biotechnol.* 2010, 30, 243-258.

2. M. W. Børsting, K. B. Qvist, M. Rasmussen, J. Vindeløv, F. K. Vogensen, Y. Ardö, Dairy Sci. 2012, 92, 593-612.

3. K. Kastberg Møller, F. P. Rattray, Y. Ardö, *J. Agric. Food Chem.* 2012, 60, 11421-11432.

4. P. L. H. McSweeney, *Int. J. Dairy Technol.* 2004, 57, 127-144.

5. J. Langholm Jensen, A. Mølgaard, J.-C. Navarro Poulsen, M. K. Harboe, J. B. Simonsen, A. M. Lorentzen, K. Hjernø, J. M. van den Brink, K. B. Qvist, S. Larsen, *Acta Cryst.* 2013, D69, 901-913.

6. S. Chitpinityol, D. Goode, M. J. C. Crabbe, *Food Chem.* 1998, 62, 133-139

7. G. L. Gilliland, E. L. Winborne, J. Nachman, A. Wlodawer, *Proteins* 1990, 8, 82-101.

8. D. S. Palmer, A. U. Christensen, J. Sørensen, L. Celik, K. Bruun Qvist, B. Schiøtt, *Biochemistry* 2010, 49, 2563-2573.

9. J. Sørensen, D. S. Palmer, B. Schiøtt, *J. Agric. Food Chem.* 2013, 61, 7949-7959.

10. I. Schechter, A. Berger, *Biochem. Biophys. Res. Commun.* 1967, 425, 497-502.

11. L. K. Creamer, N. F. Olsen, J. Food Sci. 1982, 47:631-636

12. N. Bansal, M. A. Drake, P. Piraino, M. L. Broe, M. Harboe, P. F. Fox, P. L. H. McSweeney, Int. Dairy J. 2009, 19:510-517.

13. A. C. Moynihan, S. Govindasamy-Lucey, J. J. Jaeggi, M. E. Johnson, J. A. Lucey, P. L. H. McSweeney, J. Dairy Sci. 2014, 97:85-96.

14. J. Ehren, S. Govindarajan, B. Moron, J. Minshull, C. Khosla, *Prot. Eng. Des. Sel.* 2008, 21, 699-707.

15. S. Govindarajan, B. Mannervik, J. A. Silverman, K. Wright, D. Regitsky, U. Hegazy, T. J. Purcell, M. Welch, J. Minshull, C. Gustafsson, *ACS Synth. Biol.* 2015, 4, 221-227.

16. M. Newman, M. Safro, C. Frazao, G. Khan, A. Zdanov, I. J. Tickle, T. L. Blundell, N. Andreeva, *J. Mol. Biol.* 1991, 221, 1295-1309.

17. E. Gustchina, L. Rumsh, L. Ginodman, P. Majer, N. Andreeva, *FEBS Lett.* 1996, 379, 60-62.

18. S. Visser, C. J. Slangen, P. J. van Rooijen, *Biochem. J.* 1987, 244, 553-558.

The invention claimed is:

1. An isolated chymosin polypeptide variant having an alteration in its amino acid sequence relative to a parent polypeptide having chymosin activity, wherein the alteration comprises a substitution, a deletion, or an insertion at amino acid position Y11 of the parent polypeptide, wherein
   (i) the amino acid position of the parent polypeptide is determined by alignment of the parent polypeptide with the polypeptide of SEQ ID NO:2 (camel chymosin),
   (ii) the parent polypeptide has at least 80% amino acid sequence identity with SEQ ID NO: 2,
   (iii) the variant has fewer than 30 amino acid alterations as compared to SEQ ID NO:2, as determined by an alignment of the amino acid sequence of the variant with the amino acid sequence of SEQ ID NO:2, and
   (iv) the isolated chymosin polypeptide variant has at least one of a higher specific clotting activity and a higher ratio of specific clotting activity to proteolytic activity ("C/P ratio") than the parent polypeptide.

2. The isolated chymosin polypeptide variant of claim 1, having an additional alteration in its amino acid sequence relative to the parent polypeptide selected from a substitution, deletion, or insertion at one or more of amino acid positions S164, D59, V309, S132, N249, Q56, M157, M256, R242, I96, H76, S273, G251, L166, K19, Y21, S74, Y243, Q280, F282, L295, N252, R254, G70, V136, L222, K231, L253, and N291 of the parent polypeptide, wherein the amino acid position of the parent polypeptide is determined by alignment of the parent polypeptide with the polypeptide of SEQ ID NO:2.

3. The isolated chymosin polypeptide variant of claim 1, wherein the variant has a C/P ratio that is at least 200% of the C/P ratio of the parent polypeptide.

4. The isolated chymosin polypeptide variant of claim 1, wherein the parent polypeptide has at least 82% amino acid sequence identity with SEQ ID NO:2.

5. The isolated chymosin polypeptide variant of claim 2, wherein the one or more additional alterations comprises one or more substitutions selected from: D59N, V309I, S132A, N249E, L166V, N249D, Q56H, M157L, M256L, R242E, I96L, H76Q, S164G, S273Y, G251D, R242D, L222V, L166I, K19T, Y21S, S74D, Y243E, N249D, S273D, Q280E, F282E, L295K, N252D, R254E, G70D, V136I, L222I, K231N, L253I and N291Q.

6. An isolated chymosin polypeptide variant according to claim 1, wherein the variant comprises substitutions selected from:
   Y11I, D59N, I96L, S164G, L166V, L222V, R242E, G251D, and L253I;
   Y11I, I96L, S164G, L222I, and R242E; and
   Y11V, K19T, D59N, I96L, S164G, L166V, L222I, R242E, G251D, and L253I.

7. A method for making an isolated chymosin polypeptide variant according to claim 1, comprising:
   (a) producing a chymosin polypeptide variant having an alteration at one or more positions in its amino acid sequence relative to the parent polypeptide, wherein the alteration is a substitution, a deletion, or an insertion at amino acid position Y11 of the parent polypeptide, and
   (b) isolating the chymosin polypeptide variant of step (a), thereby obtaining the isolated chymosin polypeptide variant, to obtain the variant; wherein:
   (i) the amino acid position of the parent polypeptide is determined by alignment of the parent polypeptide with SEQ ID NO:2 (camel chymosin);
   (ii) the parent polypeptide has at least 80% amino acid sequence identity with SEQ ID NO:2, and
   (iii) the variant has fewer than 30 amino acid alterations as compared to SEQ ID NO:2, as determined by an alignment of the amino acid sequence of the variant with the amino acid sequence of SEQ ID NO:2.

8. The method of claim 7, wherein the alteration is selected from: Y11I and Y11V.

9. The method according to claim 7, wherein the variant has an additional alteration in its amino acid sequence relative to the parent polypeptide selected from a substitution, deletion, or insertion at one or more of amino acid positions S164, D59, V309, S132, N249, Q56, M157, M256, R242, I96, H76, S273, G251, L166, K19, Y21, S74, Y243, Q280, F282, L295, N252, R254, G70, V136, L222, K231, L253 and N291 of the parent polypeptide, wherein the amino acid position of the parent polypeptide is determined by alignment of the parent polypeptide with the polypeptide of SEQ ID NO:2.

10. The method of claim 7, wherein the parent polypeptide has at least 95% amino acid sequence identity with SEQ ID NO:2.

11. A method for making a food or feed product comprising adding an effective amount of the isolated chymosin polypeptide variant according to claim 1 to the food or feed ingredient(s).

12. A method according to claim 11, wherein the food or feed product is a milk-based product.

13. A method according to claim 11, wherein the food or feed product is a cheese.

14. A method according to claim 13, wherein the cheese is selected from Pasta filata, Cheddar, and Continental-type cheeses.

15. A method according to claim 13, wherein the cheese is Soft Cheese or White Brine Cheese.

16. A food or feed product comprising a chymosin polypeptide variant according to claim 1.

17. The isolated chymosin polypeptide variant of claim 1, wherein the alteration is selected from Y11I and Y11V.

18. The method according to claim 9 wherein the variant comprises substitutions selected from:
- Y11I, D59N, I96L, S164G, L166V, L222V, R242E, G251D, and L253I;
- Y11I, I96L, S164G, L222I, and R242E; and
- Y11V, K19T, D59N, I96L, S164G, L166V, L222I, R242E, G251D, and L253I.

19. The method of claim 9, wherein the one or more additional alterations comprises one or more substitutions selected from: S164G, L253I, D59N, V309I, S132A, N249E, L166V, N249D, Q56H, M157L, M256L, R242E, I96L, H76Q, S273Y, G251D, R242D, L222V, L166I, K19T, Y21S, S74D, Y243E, N249D, S273D, Q280E, F282E, L295K, N252D, R254E, G70D, V136I, L222I, K231N, and N291Q.

* * * * *

SEQUENCE LISTING

<160> NUMBER OF SEQ ID NOS: 11

<210> SEQ ID NO 1
<211> LENGTH: 969
<212> TYPE: DNA
<213> ORGANISM: Camelus

<400> SEQUENCE: 1

```
gggaaggtgg ccagggaacc cctgaccagc tacctggata gtcagtactt tgggaagatc        60
tacatcggga ccccacccca ggagttcacc gtggtgtttg acactggctc ctctgacctg       120
tgggtgccct ctatctactg caagagcaat gtctgcaaaa accaccaccg ctttgacccg       180
agaaagtcgt ccaccttccg gaacctgggc aagcccctgt ccatccatta cggcacgggc       240
agcatggagg gctttctggg ctacgacacc gtcaccgtct ccaacattgt ggaccccaac       300
cagactgtgg gcctgagcac cgagcaacct ggcgaggtct tcacctactc cgagtttgac       360
gggatcctgg ggctggccta ccctcgcttg cctccgagt actcggtgcc cgtgtttgac        420
aatatgatgg acagacacct ggtggcccga gacctgttct cggtttacat ggacaggaat       480
ggccagggga gcatgcttac actggggggcc attgacccgt cctactacac cggctccctg       540
cactgggtgc ccgtgacctt gcagcagtac tggcagttca ccgtggacag tgtcaccatc       600 aacgggggtgg cagtggcctg tgttggtggc tgtcaggcca tcctggacac gggtacctcc       660
gtgctgttcg ggcccagcag cgacatcctc aaaattcaga tggctattgg agccacagag       720
aaccgatatg tgagtttga cgtcaactgt gggaacctga ggagcatgcc caccgtggtc        780
ttcgagatca atggcagaga ctacccactg tccccctccg cctacacaag caaggaccag       840
ggcttctgca ccagtggctt tcaaggtgac aacaattccg agctgtggat cctgggggat       900
gtcttcatcc gggagtatta cagtgtcttt gacagggcca caatcgcgt gggctggcc        960 aaggccatc                                                              969
```

<210> SEQ ID NO 2
<211> LENGTH: 323
<212> TYPE: PRT
<213> ORGANISM: Camelus

<400> SEQUENCE: 2

```
Gly Lys Val Ala Arg Glu Pro Leu Thr Ser Tyr Leu Asp Ser Gln Tyr
1               5                   10                  15

Phe Gly Lys Ile Tyr Ile Gly Thr Pro Pro Gln Glu Phe Thr Val Val
            20                  25                  30

Phe Asp Thr Gly Ser Ser Asp Leu Trp Val Pro Ser Ile Tyr Cys Lys
        35                  40                  45

Ser Asn Val Cys Lys Asn His His Arg Phe Asp Pro Arg Lys Ser Ser
    50                  55                  60

Thr Phe Arg Asn Leu Gly Lys Pro Leu Ser Ile His Tyr Gly Thr Gly
65                  70                  75                  80

Ser Met Glu Gly Phe Leu Gly Tyr Asp Thr Val Thr Val Ser Asn Ile
                85                  90                  95

Val Asp Pro Asn Gln Thr Val Gly Leu Ser Thr Glu Gln Pro Gly Glu
            100                 105                 110

Val Phe Thr Tyr Ser Glu Phe Asp Gly Ile Leu Gly Leu Ala Tyr Pro
        115                 120                 125

Ser Leu Ala Ser Glu Tyr Ser Val Pro Val Phe Asp Asn Met Met Asp
    130                 135                 140
```

Arg His Leu Val Ala Arg Asp Leu Phe Ser Val Tyr Met Asp Arg Asn
145                 150                 155                 160

Gly Gln Gly Ser Met Leu Thr Leu Gly Ala Ile Asp Pro Ser Tyr Tyr
                165                 170                 175

Thr Gly Ser Leu His Trp Val Pro Val Thr Leu Gln Gln Tyr Trp Gln
            180                 185                 190

Phe Thr Val Asp Ser Val Thr Ile Asn Gly Val Ala Val Ala Cys Val
        195                 200                 205

Gly Gly Cys Gln Ala Ile Leu Asp Thr Gly Thr Ser Val Leu Phe Gly
    210                 215                 220

Pro Ser Ser Asp Ile Leu Lys Ile Gln Met Ala Ile Gly Ala Thr Glu
225                 230                 235                 240

Asn Arg Tyr Gly Glu Phe Asp Val Asn Cys Gly Asn Leu Arg Ser Met
                245                 250                 255

Pro Thr Val Val Phe Glu Ile Asn Gly Arg Asp Tyr Pro Leu Ser Pro
            260                 265                 270

Ser Ala Tyr Thr Ser Lys Asp Gln Gly Phe Cys Thr Ser Gly Phe Gln
        275                 280                 285

Gly Asp Asn Asn Ser Glu Leu Trp Ile Leu Gly Asp Val Phe Ile Arg
    290                 295                 300

Glu Tyr Tyr Ser Val Phe Asp Arg Ala Asn Asn Arg Val Gly Leu Ala
305                 310                 315                 320

Lys Ala Ile

<210> SEQ ID NO 3
<211> LENGTH: 323
<212> TYPE: PRT
<213> ORGANISM: Bos

<400> SEQUENCE: 3

Gly Glu Val Ala Ser Val Pro Leu Thr Asn Tyr Leu Asp Ser Gln Tyr
1               5                   10                  15

Phe Gly Lys Ile Tyr Leu Gly Thr Pro Pro Gln Glu Phe Thr Val Leu
                20                  25                  30

Phe Asp Thr Gly Ser Ser Asp Phe Trp Val Pro Ser Ile Tyr Cys Lys
            35                  40                  45

Ser Asn Ala Cys Lys Asn His Gln Arg Phe Asp Pro Arg Lys Ser Ser
        50                  55                  60

Thr Phe Gln Asn Leu Gly Lys Pro Leu Ser Ile His Tyr Gly Thr Gly
65                  70                  75                  80

Ser Met Gln Gly Ile Leu Gly Tyr Asp Thr Val Thr Val Ser Asn Ile
                85                  90                  95

Val Asp Ile Gln Gln Thr Val Gly Leu Ser Thr Gln Glu Pro Gly Asp
            100                 105                 110

Val Phe Thr Tyr Ala Glu Phe Asp Gly Ile Leu Gly Met Ala Tyr Pro
        115                 120                 125

Ser Leu Ala Ser Glu Tyr Ser Ile Pro Val Phe Asp Asn Met Met Asn
    130                 135                 140

Arg His Leu Val Ala Gln Asp Leu Phe Ser Val Tyr Met Asp Arg Asn
145                 150                 155                 160

Gly Gln Glu Ser Met Leu Thr Leu Gly Ala Ile Asp Pro Ser Tyr Tyr
                165                 170                 175

Thr Gly Ser Leu His Trp Val Pro Val Thr Val Gln Gln Tyr Trp Gln
            180                 185                 190

```
Phe Thr Val Asp Ser Val Thr Ile Ser Gly Val Val Ala Cys Glu
            195                 200                 205

Gly Gly Cys Gln Ala Ile Leu Asp Thr Gly Thr Ser Lys Leu Val Gly
210                 215                 220

Pro Ser Ser Asp Ile Leu Asn Ile Gln Gln Ala Ile Gly Ala Thr Gln
225                 230                 235                 240

Asn Gln Tyr Gly Glu Phe Asp Ile Asp Cys Asp Asn Leu Ser Tyr Met
                245                 250                 255

Pro Thr Val Val Phe Glu Ile Asn Gly Lys Met Tyr Pro Leu Thr Pro
                260                 265                 270

Ser Ala Tyr Thr Ser Gln Asp Gln Gly Phe Cys Thr Ser Gly Phe Gln
            275                 280                 285

Ser Glu Asn His Ser Gln Lys Trp Ile Leu Gly Asp Val Phe Ile Arg
            290                 295                 300

Glu Tyr Tyr Ser Val Phe Asp Arg Ala Asn Asn Leu Val Gly Leu Ala
305                 310                 315                 320

Lys Ala Ile
```

<210> SEQ ID NO 4
<211> LENGTH: 1095
<212> TYPE: DNA
<213> ORGANISM: Camelus

<400> SEQUENCE: 4

```
agtgggatca ccaggatccc tctgcacaaa ggcaagactc tgagaaaagc gctgaaggag      60
cgtgggctcc tggaggactt tctgcagaga caacagtatg ccgtcagcag caagtactcc     120
agcttgggga aggtggccag ggaacccctg accagctacc tggatagtca gtactttggg     180
aagatctaca tcgggacccc acccaggag ttcaccgtgg tgtttgacac tggctcctct      240
gacctgtggg tgccctctat ctactgcaag agcaatgtct gcaaaaacca ccaccgcttt     300
gacccgagaa agtcgtccac cttccggaac ctgggcaagc cctgtccat ccattacggc      360
acgggcagca tggagggctt tctgggctac gacaccgtca ccgtctccaa cattgtggac     420
cccaaccaga ctgtgggcct gagcaccgag caacctggcg aggtcttcac ctactccgag     480
tttgacggga tcctggggct ggcctacccc tcgcttgcct ccgagtactc ggtgcccgtg     540
tttgacaata tgatggacag acacctggtg gcccgagacc tgttctcggt ttacatggac     600
aggaatggcc aggggagcat gcttacactg ggggccattg acccgtccta ctacaccggc     660
tccctgcact gggtgcccgt gaccttgcag cagtactggc agttcaccgt ggacagtgtc     720
accatcaacg gggtggcagt ggcctgtgtt ggtggctgtc aggccatcct ggacacgggt     780
acctccgtgc tgttcgggcc cagcagcgac atcctcaaaa ttcagatggc tattggagcc     840
acagagaacc gatatggtga gtttgacgtc aactgtggga acctgaggag catgcccacc     900
gtggtcttcg agatcaatgg cagagactac ccactgtccc cctccgccta cacaagcaag     960
gaccagggct tctgcaccag tggctttcaa ggtgacaaca attccgagct gtggatcctg    1020
ggggatgtct tcatccggga gtattacagt gtctttgaca gggccaacaa tcgcgtgggg    1080
ctggccaagg ccatc                                                     1095
```

<210> SEQ ID NO 5
<211> LENGTH: 365
<212> TYPE: PRT
<213> ORGANISM: Camelus

<400> SEQUENCE: 5

```
Ser Gly Ile Thr Arg Ile Pro Leu His Lys Gly Lys Thr Leu Arg Lys
1               5                   10                  15

Ala Leu Lys Glu Arg Gly Leu Leu Glu Asp Phe Leu Gln Arg Gln Gln
            20                  25                  30

Tyr Ala Val Ser Ser Lys Tyr Ser Ser Leu Gly Lys Val Ala Arg Glu
        35                  40                  45

Pro Leu Thr Ser Tyr Leu Asp Ser Gln Tyr Phe Gly Lys Ile Tyr Ile
    50                  55                  60

Gly Thr Pro Pro Gln Glu Phe Thr Val Val Phe Asp Thr Gly Ser Ser
65                  70                  75                  80

Asp Leu Trp Val Pro Ser Ile Tyr Cys Lys Ser Asn Val Cys Lys Asn
                85                  90                  95

His His Arg Phe Asp Pro Arg Lys Ser Ser Thr Phe Arg Asn Leu Gly
                100                 105                 110

Lys Pro Leu Ser Ile His Tyr Gly Thr Gly Ser Met Glu Gly Phe Leu
            115                 120                 125

Gly Tyr Asp Thr Val Thr Val Ser Asn Ile Val Asp Pro Asn Gln Thr
130                 135                 140

Val Gly Leu Ser Thr Glu Gln Pro Gly Glu Val Phe Thr Tyr Ser Glu
145                 150                 155                 160

Phe Asp Gly Ile Leu Gly Leu Ala Tyr Pro Ser Leu Ala Ser Glu Tyr
                165                 170                 175

Ser Val Pro Val Phe Asp Asn Met Met Asp Arg His Leu Val Ala Arg
                180                 185                 190

Asp Leu Phe Ser Val Tyr Met Asp Arg Asn Gly Gln Gly Ser Met Leu
                195                 200                 205

Thr Leu Gly Ala Ile Asp Pro Ser Tyr Tyr Thr Gly Ser Leu His Trp
210                 215                 220

Val Pro Val Thr Leu Gln Gln Tyr Trp Gln Phe Thr Val Asp Ser Val
225                 230                 235                 240

Thr Ile Asn Gly Val Ala Val Ala Cys Val Gly Gly Cys Gln Ala Ile
                245                 250                 255

Leu Asp Thr Gly Thr Ser Val Leu Phe Gly Pro Ser Ser Asp Ile Leu
                260                 265                 270

Lys Ile Gln Met Ala Ile Gly Ala Thr Glu Asn Arg Tyr Gly Glu Phe
            275                 280                 285

Asp Val Asn Cys Gly Asn Leu Arg Ser Met Pro Thr Val Val Phe Glu
            290                 295                 300

Ile Asn Gly Arg Asp Tyr Pro Leu Ser Pro Ser Ala Tyr Thr Ser Lys
305                 310                 315                 320

Asp Gln Gly Phe Cys Thr Ser Gly Phe Gln Gly Asp Asn Asn Ser Glu
                325                 330                 335

Leu Trp Ile Leu Gly Asp Val Phe Ile Arg Glu Tyr Tyr Ser Val Phe
                340                 345                 350

Asp Arg Ala Asn Asn Arg Val Gly Leu Ala Lys Ala Ile
                355                 360                 365

<210> SEQ ID NO 6
<211> LENGTH: 379
<212> TYPE: PRT
<213> ORGANISM: Rattus
<223> OTHER INFORMATION: From figure 1
<220> FEATURE:
<223> OTHER INFORMATION: From figure 1
```

<400> SEQUENCE: 6

```
Met Arg Cys Phe Val Leu Leu Leu Ala Val Leu Ala Ile Ala Gln Ser
1               5                   10                  15

His Val Val Thr Arg Ile Pro Leu His Lys Gly Lys Ser Leu Arg Asn
            20                  25                  30

Thr Leu Lys Glu Gln Gly Leu Leu Glu Asp Phe Leu Arg His Gln
        35                  40                  45

Tyr Glu Phe Ser Glu Lys Asn Ser Asn Ile Gly Met Val Ala Ser Glu
    50                  55                  60

Pro Leu Thr Asn Tyr Leu Asp Ser Glu Tyr Phe Gly Leu Ile Tyr Val
65                  70                  75                  80

Gly Thr Pro Pro Gln Glu Phe Lys Val Val Phe Asp Thr Gly Ser Ser
                85                  90                  95

Glu Leu Trp Val Pro Ser Val Tyr Cys Ser Ser Lys Val Cys Arg Asn
                100                 105                 110

His Asn Arg Phe Asp Pro Ser Lys Ser Phe Thr Phe Gln Asn Leu Ser
            115                 120                 125

Lys Pro Leu Phe Val Gln Tyr Gly Thr Gly Ser Val Glu Gly Phe Leu
        130                 135                 140

Ala Tyr Asp Thr Val Thr Val Ser Asp Ile Val Val Pro His Gln Thr
145                 150                 155                 160

Val Gly Leu Ser Thr Glu Glu Pro Gly Asp Ile Phe Thr Tyr Ser Pro
                165                 170                 175

Phe Asp Gly Ile Leu Gly Leu Ala Tyr Pro Thr Phe Ala Ser Lys Tyr
            180                 185                 190

Ser Val Pro Ile Phe Asp Asn Met Met Asn Arg His Leu Val Ala Gln
        195                 200                 205

Asp Leu Phe Ser Val Tyr Met Ser Arg Asn Asp Gln Gly Ser Met Leu
    210                 215                 220

Thr Leu Gly Ala Ile Asp Gln Ser Tyr Phe Ile Gly Ser Leu His Trp
225                 230                 235                 240

Val Pro Val Thr Val Gln Gly Tyr Trp Gln Phe Thr Val Asp Arg Ile
                245                 250                 255

Thr Ile Asn Asp Glu Val Val Ala Cys Gln Gly Gly Cys Pro Ala Val
            260                 265                 270

Leu Asp Thr Gly Thr Ala Leu Leu Thr Gly Pro Gly Arg Asp Ile Leu
        275                 280                 285

Asn Ile Gln His Ala Ile Gly Ala Val Gln Gly His Asp Gln Phe
    290                 295                 300

Asp Ile Asp Cys Trp Arg Leu Asn Phe Met Pro Thr Val Val Phe Glu
305                 310                 315                 320

Ile Asn Gly Arg Glu Phe Pro Leu Pro Pro Ser Ala Tyr Thr Asn Gln
                325                 330                 335

Phe Gln Gly Ser Cys Ser Ser Gly Phe Arg His Gly Ser Gln Met Trp
            340                 345                 350

Ile Leu Gly Asp Val Phe Ile Arg Glu Phe Tyr Ser Val Phe Asp Arg
        355                 360                 365

Ala Asn Asn Arg Val Gly Leu Ala Lys Ala Ile
    370                 375
```

<210> SEQ ID NO 7
<211> LENGTH: 380
<212> TYPE: PRT
<213> ORGANISM: Sus

<223> OTHER INFORMATION: From figure 1
<220> FEATURE:
<223> OTHER INFORMATION: From figure 1

<400> SEQUENCE: 7

```
Ile Arg Gly Arg Val Leu Leu Ala Val Leu Ala Leu Ser Gln Gly Ser
1               5                   10                  15

Gly Ile Thr Arg Val Pro Leu Arg Lys Gly Lys Ser Leu Arg Lys Glu
            20                  25                  30

Leu Lys Glu Arg Gly Leu Leu Glu Asp Phe Leu Gln Lys Gln Pro Tyr
        35                  40                  45

Ala Leu Ser Ser Lys Tyr Ser Ser Phe Gly Glu Val Ala Ser Glu Pro
    50                  55                  60

Leu Thr Asn Tyr Leu Asp Thr Gln Tyr Phe Gly Lys Ile Tyr Ile Gly
65                  70                  75                  80

Thr Pro Pro Gln Glu Phe Thr Val Val Phe Asp Thr Gly Ser Ser Glu
                85                  90                  95

Leu Trp Val Pro Ser Val Tyr Cys Lys Ser Asp Ala Cys Gln Asn His
            100                 105                 110

His Arg Phe Asn Pro Ser Lys Ser Ser Thr Phe Gln Asn Leu Asp Lys
        115                 120                 125

Pro Leu Ser Ile Gln Tyr Gly Thr Gly Ser Ile Gln Gly Phe Leu Gly
    130                 135                 140

Tyr Asp Thr Val Met Val Ala Gly Ile Val Asp Ala His Gln Thr Val
145                 150                 155                 160

Gly Leu Ser Thr Gln Glu Pro Ser Asp Ile Phe Thr Tyr Ser Glu Phe
                165                 170                 175

Asp Gly Ile Leu Gly Leu Gly Tyr Pro Glu Leu Ala Ser Glu Tyr Thr
            180                 185                 190

Val Pro Val Phe Asp Asn Met Met His Arg His Leu Val Ala Gln Asp
        195                 200                 205

Leu Phe Ala Val Tyr Met Ser Arg Asn Asp Glu Gly Ser Met Leu Thr
    210                 215                 220

Leu Gly Ala Ile Asp Pro Ser Tyr Tyr Thr Gly Ser Leu His Trp Val
225                 230                 235                 240

Pro Val Thr Met Gln Leu Tyr Trp Gln Phe Thr Val Asp Ser Val Thr
                245                 250                 255

Ile Asn Gly Val Val Ala Cys Asn Gly Cys Gln Ala Ile Leu
            260                 265                 270

Asp Thr Gly Thr Ser Met Leu Ala Gly Pro Ser Ser Asp Ile Leu Asn
        275                 280                 285

Ile Gln Met Ala Ile Gly Ala Thr Glu Ser Gln Tyr Gly Glu Phe Asp
    290                 295                 300

Ile Asp Cys Gly Ser Leu Ser Ser Met Pro Thr Val Val Phe Glu Ile
305                 310                 315                 320

Ser Gly Arg Met Tyr Pro Leu Pro Pro Ser Ala Tyr Thr Asn Gln Asp
                325                 330                 335

Gln Gly Phe Cys Thr Ser Gly Phe Gln Gly Asp Ser Lys Ser Gln Met
            340                 345                 350

Trp Ile Leu Gly Asp Val Phe Ile Arg Glu Phe Tyr Ser Val Phe Asp
        355                 360                 365

Arg Ala Asn Asn Arg Val Gly Leu Ala Lys Ala Ile
    370                 375                 380
```

```
<210> SEQ ID NO 8
<211> LENGTH: 381
<212> TYPE: PRT
<213> ORGANISM: Camelus dromedarius
<223> OTHER INFORMATION: from figure 1
<220> FEATURE:
<223> OTHER INFORMATION: from figure 1

<400> SEQUENCE: 8

Met Arg Cys Leu Val Val Leu Leu Ala Ala Leu Ala Leu Ser Gln Ala
1               5                   10                  15

Ser Gly Ile Thr Arg Ile Pro Leu His Lys Gly Lys Thr Leu Arg Lys
            20                  25                  30

Ala Leu Lys Glu Arg Gly Leu Leu Glu Asp Phe Leu Gln Arg Gln Gln
        35                  40                  45

Tyr Ala Val Ser Ser Lys Tyr Ser Ser Leu Gly Lys Val Ala Arg Glu
    50                  55                  60

Pro Leu Thr Ser Tyr Leu Asp Ser Gln Tyr Phe Gly Lys Ile Tyr Ile
65                  70                  75                  80

Gly Thr Pro Pro Gln Glu Phe Thr Val Val Phe Asp Thr Gly Ser Ser
                85                  90                  95

Asp Leu Trp Val Pro Ser Ile Tyr Cys Lys Ser Asn Val Cys Lys Asn
            100                 105                 110

His His Arg Phe Asp Pro Arg Lys Ser Ser Thr Phe Arg Asn Leu Gly
        115                 120                 125

Lys Pro Leu Ser Ile His Tyr Gly Thr Gly Ser Met Glu Gly Phe Leu
    130                 135                 140

Gly Tyr Asp Thr Val Thr Val Ser Asn Ile Val Asp Pro Asn Gln Thr
145                 150                 155                 160

Val Gly Leu Ser Thr Glu Gln Pro Gly Glu Val Phe Thr Tyr Ser Glu
                165                 170                 175

Phe Asp Gly Ile Leu Gly Leu Ala Tyr Pro Ser Leu Ala Ser Glu Tyr
            180                 185                 190

Ser Val Pro Val Phe Asp Asn Met Met Asp Arg His Leu Val Ala Arg
        195                 200                 205

Asp Leu Phe Ser Val Tyr Met Asp Arg Asn Gly Gln Gly Ser Met Leu
    210                 215                 220

Thr Leu Gly Ala Ile Asp Pro Ser Tyr Tyr Thr Gly Ser Leu His Trp
225                 230                 235                 240

Val Pro Val Thr Leu Gln Gln Tyr Trp Gln Phe Thr Val Asp Ser Val
                245                 250                 255

Thr Ile Asn Gly Val Ala Val Ala Cys Val Gly Cys Gln Ala Ile
            260                 265                 270

Leu Asp Thr Gly Thr Ser Val Leu Phe Gly Pro Ser Ser Asp Ile Leu
        275                 280                 285

Lys Ile Gln Met Ala Ile Gly Ala Thr Glu Asn Arg Tyr Gly Glu Phe
    290                 295                 300

Asp Val Asn Cys Gly Asn Leu Arg Ser Met Pro Thr Val Val Phe Glu
305                 310                 315                 320

Ile Asn Gly Arg Asp Tyr Pro Leu Ser Pro Ser Ala Tyr Thr Ser Lys
                325                 330                 335

Asp Gln Gly Phe Cys Thr Ser Gly Phe Gln Gly Asp Asn Asn Ser Glu
            340                 345                 350

Leu Trp Ile Leu Gly Asp Val Phe Ile Arg Glu Tyr Tyr Ser Val Phe
        355                 360                 365
```

Asp Arg Ala Asn Asn Arg Val Gly Leu Ala Lys Ala Ile
        370                 375                 380

<210> SEQ ID NO 9
<211> LENGTH: 381
<212> TYPE: PRT
<213> ORGANISM: Camelus bactrianus
<223> OTHER INFORMATION: From figure 1
<220> FEATURE:
<223> OTHER INFORMATION: From figure 1

<400> SEQUENCE: 9

Met Arg Cys Leu Val Val Leu Ala Ala Leu Ala Leu Ser Gln Ala
1               5                   10                  15

Ser Gly Ile Thr Arg Ile Pro Leu His Lys Gly Lys Thr Leu Arg Lys
            20                  25                  30

Ala Leu Lys Glu Arg Gly Leu Leu Glu Asp Phe Leu Gln Arg Gln Gln
        35                  40                  45

Tyr Ala Val Ser Ser Lys Tyr Ser Ser Leu Gly Lys Val Ala Arg Glu
    50                  55                  60

Pro Leu Thr Ser Tyr Leu Asp Ser Gln Tyr Phe Gly Lys Ile Tyr Ile
65                  70                  75                  80

Gly Thr Pro Pro Gln Glu Phe Thr Val Val Phe Asp Thr Gly Ser Ser
                85                  90                  95

Asp Leu Trp Val Pro Ser Ile Tyr Cys Lys Ser Asn Ala Cys Lys Asn
            100                 105                 110

His His Arg Phe Asp Pro Arg Lys Ser Ser Thr Phe Arg Asn Leu Gly
        115                 120                 125

Lys Pro Leu Ser Ile His Tyr Gly Thr Gly Ser Ile Glu Gly Phe Leu
    130                 135                 140

Gly Tyr Asp Thr Val Thr Val Ser Asn Ile Val Asp Pro Asn Gln Thr
145                 150                 155                 160

Val Gly Leu Ser Thr Glu Gln Pro Gly Glu Val Phe Thr Tyr Ser Glu
                165                 170                 175

Phe Asp Gly Ile Leu Gly Leu Ala Tyr Pro Ser Leu Ala Ser Glu Tyr
            180                 185                 190

Ser Val Pro Val Phe Asp Asn Met Met Asp Arg His Leu Val Ala Arg
        195                 200                 205

Asp Leu Phe Ser Val Tyr Met Asp Arg Asn Gly Gln Gly Ser Met Leu
    210                 215                 220

Thr Leu Gly Ala Thr Asp Pro Ser Tyr Tyr Thr Gly Ser Leu His Trp
225                 230                 235                 240

Val Pro Val Thr Val Gln Gln Tyr Trp Gln Val Thr Val Asp Ser Val
                245                 250                 255

Thr Ile Asn Gly Val Ala Val Ala Cys Val Gly Cys Gln Ala Ile
            260                 265                 270

Leu Asp Thr Gly Thr Ser Val Leu Phe Gly Pro Ser Ser Asp Ile Leu
        275                 280                 285

Lys Ile Gln Met Ala Ile Gly Ala Thr Glu Asn Arg Tyr Gly Glu Phe
    290                 295                 300

Asp Val Asn Cys Gly Ser Leu Arg Ser Met Pro Thr Val Phe Glu
305                 310                 315                 320

Ile Asn Gly Arg Asp Phe Pro Leu Ala Pro Ser Ala Tyr Thr Ser Lys
                325                 330                 335

Asp Gln Gly Phe Cys Thr Ser Gly Phe Gln Gly Asp Asn Asn Ser Glu
            340                 345                 350

Leu Trp Ile Leu Gly Asp Val Phe Ile Arg Glu Tyr Tyr Ser Val Phe
        355                 360                 365

Asp Arg Ala Asn Asn Arg Val Gly Leu Ala Lys Ala Ile
370                 375                 380

<210> SEQ ID NO 10
<211> LENGTH: 381
<212> TYPE: PRT
<213> ORGANISM: Ovis
<223> OTHER INFORMATION: From figure 1
<220> FEATURE:
<223> OTHER INFORMATION: From figure 1

<400> SEQUENCE: 10

Met Arg Cys Leu Val Val Leu Ala Val Phe Ala Leu Ser Gln Gly
1               5                   10                  15

Ala Glu Ile Thr Arg Ile Pro Leu Tyr Lys Gly Lys Pro Leu Arg Lys
            20                  25                  30

Ala Leu Lys Glu Arg Gly Leu Leu Glu Asp Phe Leu Gln Lys Gln Gln
        35                  40                  45

Tyr Gly Val Ser Ser Glu Tyr Ser Gly Phe Gly Glu Val Ala Ser Val
50                  55                  60

Pro Leu Thr Asn Tyr Leu Asp Ser Gln Tyr Phe Gly Lys Ile Tyr Leu
65                  70                  75                  80

Gly Thr Pro Pro Gln Glu Phe Thr Val Leu Phe Asp Thr Gly Ser Ser
                85                  90                  95

Asp Phe Trp Val Pro Ser Ile Tyr Cys Lys Ser Asn Ala Cys Lys Asn
            100                 105                 110

His Gln Arg Phe Asp Pro Arg Lys Ser Ser Thr Phe Gln Asn Leu Gly
        115                 120                 125

Lys Pro Leu Ser Ile Arg Tyr Gly Thr Gly Ser Met Gln Gly Ile Leu
130                 135                 140

Gly Tyr Asp Thr Val Thr Val Ser Asn Ile Val Asp Ile Gln Gln Thr
145                 150                 155                 160

Val Gly Leu Ser Thr Gln Glu Pro Gly Asp Val Phe Thr Tyr Ala Glu
                165                 170                 175

Phe Asp Gly Ile Leu Gly Met Ala Tyr Pro Ser Leu Ala Ser Glu Tyr
            180                 185                 190

Ser Val Pro Val Phe Asp Asn Met Met Asp Arg Arg Leu Val Ala Gln
        195                 200                 205

Asp Leu Phe Ser Val Tyr Met Asp Arg Ser Gly Gln Gly Ser Met Leu
210                 215                 220

Thr Leu Gly Ala Ile Asp Pro Ser Tyr Tyr Thr Gly Ser Leu His Trp
225                 230                 235                 240

Val Pro Val Thr Leu Gln Lys Tyr Trp Gln Phe Thr Val Asp Ser Val
                245                 250                 255

Thr Ile Ser Gly Ala Val Val Ala Cys Glu Gly Cys Gln Ala Ile
            260                 265                 270

Leu Asp Thr Gly Thr Ser Lys Leu Val Gly Pro Ser Ser Asp Ile Leu
        275                 280                 285

Asn Ile Gln Gln Ala Ile Gly Ala Thr Gln Asn Gln Tyr Gly Glu Phe
290                 295                 300

Asp Ile Asp Cys Asp Ser Leu Ser Ser Met Pro Thr Val Val Phe Glu
305                 310                 315                 320

Ile Asn Gly Lys Met Tyr Pro Leu Thr Pro Tyr Ala Tyr Thr Ser Gln

```
                    325                 330                 335
Glu Glu Gly Phe Cys Thr Ser Gly Phe Gln Gly Glu Asn His Ser His
                340                 345                 350
Gln Trp Ile Leu Gly Asp Val Phe Ile Arg Glu Tyr Tyr Ser Val Phe
            355                 360                 365
Asp Arg Ala Asn Asn Leu Val Gly Leu Ala Lys Ala Ile
        370                 375                 380

<210> SEQ ID NO 11
<211> LENGTH: 382
<212> TYPE: PRT
<213> ORGANISM: Bos
<223> OTHER INFORMATION: From figure 1
<220> FEATURE:
<223> OTHER INFORMATION: From figure 1

<400> SEQUENCE: 11

Asx Met Arg Cys Leu Val Val Leu Leu Ala Val Phe Ala Leu Ser Gln
1               5                   10                  15
Gly Ala Glu Ile Thr Arg Ile Pro Leu Tyr Lys Gly Lys Ser Leu Arg
            20                  25                  30
Lys Ala Leu Lys Glu His Gly Leu Leu Glu Asp Phe Leu Gln Lys Gln
        35                  40                  45
Gln Tyr Gly Ile Ser Ser Lys Tyr Ser Gly Phe Gly Glu Val Ala Ser
    50                  55                  60
Val Pro Leu Thr Asn Tyr Leu Asp Ser Gln Tyr Phe Gly Lys Ile Tyr
65                  70                  75                  80
Leu Gly Thr Pro Pro Gln Glu Phe Thr Val Leu Phe Asp Thr Gly Ser
                85                  90                  95
Ser Asp Phe Trp Val Pro Ser Ile Tyr Cys Lys Ser Asn Ala Cys Lys
            100                 105                 110
Asn His Gln Arg Phe Asp Pro Arg Lys Ser Ser Thr Phe Gln Asn Leu
        115                 120                 125
Gly Lys Pro Leu Ser Ile His Tyr Gly Thr Gly Ser Met Gln Gly Ile
    130                 135                 140
Leu Gly Tyr Asp Thr Val Thr Val Ser Asn Ile Val Asp Ile Gln Gln
145                 150                 155                 160
Thr Val Gly Leu Ser Thr Gln Glu Pro Gly Asp Val Phe Thr Tyr Ala
                165                 170                 175
Glu Phe Asp Gly Ile Leu Gly Met Ala Tyr Pro Ser Leu Ala Ser Glu
            180                 185                 190
Tyr Ser Ile Pro Val Phe Asp Asn Met Met Asn Arg His Leu Val Ala
        195                 200                 205
Gln Asp Leu Phe Ser Val Tyr Met Asp Arg Asn Gly Gln Glu Ser Met
    210                 215                 220
Leu Thr Leu Gly Ala Ile Asp Pro Ser Tyr Tyr Thr Gly Ser Leu His
225                 230                 235                 240
Trp Val Pro Val Thr Val Gln Gln Tyr Trp Gln Phe Thr Val Asp Ser
                245                 250                 255
Val Thr Ile Ser Gly Val Val Ala Cys Glu Gly Gly Cys Gln Ala
            260                 265                 270
Ile Leu Asp Thr Gly Thr Ser Lys Leu Val Gly Pro Ser Ser Asp Ile
        275                 280                 285
Leu Asn Ile Gln Gln Ala Ile Gly Ala Thr Gln Asn Gln Tyr Gly Glu
    290                 295                 300
```

```
Phe Asp Ile Asp Cys Asp Asn Leu Ser Tyr Met Pro Thr Val Val Phe
305             310                 315                 320

Glu Ile Asn Gly Lys Met Tyr Pro Leu Thr Pro Ser Ala Tyr Thr Ser
                325                 330                 335

Gln Asp Gln Gly Phe Cys Thr Ser Gly Phe Gln Ser Glu Asn His Ser
                340                 345                 350

Gln Lys Trp Ile Leu Gly Asp Val Phe Ile Arg Glu Tyr Tyr Ser Val
            355                 360                 365

Phe Asp Arg Ala Asn Asn Leu Val Gly Leu Ala Lys Ala Ile
            370                 375                 380
```